US012397092B2

(12) United States Patent
Boddie

(10) Patent No.: US 12,397,092 B2
(45) Date of Patent: Aug. 26, 2025

(54) BREAST PUMPING SYSTEM

(71) Applicant: RESTFUL PUMP, INC., Pembroke, MA (US)

(72) Inventor: Micolene Boddie, Pembroke, MA (US)

(73) Assignee: RESTFUL PUMP, INC., Pembroke, MA (US)

( * ) Notice: Subject to any disclaimer, the term of this patent is extended or adjusted under 35 U.S.C. 154(b) by 624 days.

(21) Appl. No.: 17/894,305

(22) Filed: Aug. 24, 2022

(65) Prior Publication Data
US 2022/0409784 A1 Dec. 29, 2022

Related U.S. Application Data

(63) Continuation-in-part of application No. 17/699,357, filed on Mar. 21, 2022, now Pat. No. 12,296,076, which is a continuation-in-part of application No. 16/851,706, filed on Apr. 17, 2020, now Pat. No. 11,793,913, which is a continuation-in-part of
(Continued)

(51) Int. Cl.
| | |
|---|---|
| *A61M 1/06* | (2006.01) |
| *A47B 37/00* | (2006.01) |
| *A47C 7/38* | (2006.01) |
| *A47C 7/50* | (2006.01) |
| *A47C 7/62* | (2006.01) |
| *A47C 9/00* | (2006.01) |
| *A47D 9/00* | (2006.01) |

(52) U.S. Cl.
CPC ............. *A61M 1/068* (2014.02); *A47B 37/00* (2013.01); *A47C 7/38* (2013.01); *A47C 7/503* (2013.01); *A47C 7/626* (2018.08); *A47C 9/005* (2013.01); *A47D 9/016* (2022.08); *A61M 1/067* (2021.05); *A61M 2209/084* (2013.01)

(58) Field of Classification Search
CPC ........ A61M 1/06; A61M 1/062; A61M 1/064; A61M 1/066; A61M 1/067; A61M 1/068; A61M 1/069; A61M 1/0693; A61M 1/06935; A61M 1/0697
See application file for complete search history.

(56) References Cited

U.S. PATENT DOCUMENTS

| | | |
|---|---|---|
| 78,472 A | 6/1868 | Neuhaus |
| 1,554,118 A | 9/1925 | Moran |

(Continued)

FOREIGN PATENT DOCUMENTS

| | | |
|---|---|---|
| CN | 203280090 | 11/2013 |
| WO | 2003/013628 | 2/2003 |

(Continued)

OTHER PUBLICATIONS

EP Application No. 20881042, Extended European Search Report, dated Nov. 3, 2023.
(Continued)

*Primary Examiner* — Dung T Ulsh
(74) *Attorney, Agent, or Firm* — Troutman Pepper Locke LLP

(57) ABSTRACT

A breast pumping assembly is provided. The assembly allows for a breast pumping mother to be optimally positioned and comfortable while pumping breast milk, leading to quicker and more effective pumping. The breast pumping assembly is adjustable to adapt for different sized mothers and changing body size and shape as pumping progresses.

19 Claims, 22 Drawing Sheets

Related U.S. Application Data application No. 16/665,448, filed on Oct. 28, 2019, now Pat. No. 11,850,340.

(56) References Cited

U.S. PATENT DOCUMENTS

| | | | |
|---|---|---|---|
| 4,552,404 | A | 11/1985 | Congleton |
| 4,589,699 | A | 5/1986 | Dungan |
| 5,149,174 | A | 9/1992 | Charash |
| 5,514,166 | A | 5/1996 | Silver et al. |
| 5,667,278 | A | 9/1997 | Li |
| 6,502,262 | B1 | 1/2003 | Piscopo |
| 7,070,241 | B2 | 7/2006 | Saulnier et al. |
| 7,540,049 | B2 | 6/2009 | Sklenarik et al. |
| 7,784,871 | B2 | 8/2010 | Cochran |
| 8,043,255 | B2 * | 10/2011 | Weston ............... A61M 1/06 604/74 |
| 8,590,968 | B2 * | 11/2013 | Zahir ................ A47C 7/543 297/440.14 |
| 9,138,072 | B1 * | 9/2015 | Sanders ............ A47G 9/0253 |
| 9,480,783 | B2 | 11/2016 | Johnson et al. |
| 2005/0235425 | A1 * | 10/2005 | Parrilla ............... A47D 13/08 5/655 |
| 2006/0265809 | A1 * | 11/2006 | Wagner .............. A47D 13/083 5/655 |
| 2007/0135761 | A1 | 6/2007 | Cheng et al. |
| 2010/0194166 | A1 | 8/2010 | Grenier |
| 2011/0315832 | A1 | 12/2011 | Box |
| 2012/0260831 | A1 | 10/2012 | McCarty |
| 2021/0121615 | A1 | 4/2021 | Boddie et al. |

FOREIGN PATENT DOCUMENTS

| | | |
|---|---|---|
| WO | 2008085174 A1 | 7/2008 |
| WO | 2009044422 | 4/2009 |
| WO | 2018/060698 | 4/2018 |

OTHER PUBLICATIONS

International Search Report and Written Opinion Dated Sep. 21, 2023. International Appln No. PCT/US2023/064608.

* cited by examiner

BREAST PUMPING SYSTEM

BACKGROUND

Technical Field

The present disclosure relates generally to breast pumping systems. More particularly the present disclosure relates to an assembly which allows a mother to lean forward in a relaxed position while using a breast pump to pump breastmilk.

Description of Related Art

Feeding infant children using breastmilk has a number of advantages from both a health, financial, and convenience perspective. In many instances, to build up a store of milk for feeding the infant, mothers will pump milk for later consumption. This advantageously allows a mother to return to work, and be away from the infant for periods of time.

However, many mothers struggle with nursing for many reasons, including providing enough milk volume to feed the growing child. This is a very common issue with various causes. Some causes of milk production shortages include stress and anxiety of caring for the infant, discomfort caused by nursing and pumping, and discomfort from the various body positions that must be maintained for extended periods of time during a pumping session. Often, during a pumping session, a woman is seated with poor posture. This can lead to sub-optimal positioning, leading to inefficient pumping, less milk extraction which may lead to infections, mastitis, and other medical conditions, and reduced milk production. Discouragement and fewer pump sessions also leads to poor milk supply.

Therefore, what is needed is breast pumping system which can allow a mother who is pumping breastmilk to rest in a comfortable and physiologically ideal position.

SUMMARY

The subject matter of this application may involve, in some cases, interrelated products, alternative solutions to a particular problem, and/or a plurality of different uses of a single system or article.

In one aspect, a breast pumping assembly is provided which is attachable to a forward-leaning chair. The assembly comprises a breast pumping table and a bottle shelf positioned below the breast pumping table. The table is sized to hold a breast pump, and has a ridge extending from a top of at least a part of its perimeter. The table further defines two openings so that a part of a bottle or breast pumping shield can pass through, so as to provide access to a bottle resting on the bottle shelf below. In other embodiments, the bottles may rest on the table, omitting a bottle shelf below. Each of the breast pump table and bottle shelf are connected to a support, which in turn is connectable to a forward-leaning chair. In other embodiments, the assembly may comprise only the breast pumping table, and bottles can be positioned thereon, instead of on a shelf below.

In another aspect, a forward-leaning breast pumping chair is provided. The chair has a center post, a seat and head rest attached thereto, and a base. The center post is angled forwardly relative to the base so that when a user sits on the seat, they are positioned to be leaning forward relative to the base and the flat ground that the base rests on. The chair further includes a breast pumping assembly attached to the center post. The assembly comprises a breast pumping table and a bottle shelf positioned below the breast pumping table. The table is sized to hold a breast pump, and has a ridge extending from a top of at least a part of its perimeter. The table further defines two openings so that a part of a bottle or breast pumping shield can pass through, so as to connect to a bottle resting on the bottle shelf below. Each of the breast pump table and bottle shelf are connected to a support, which in turn is connected to the forward-leaning chair.

DETAILED DESCRIPTION

Figure 1:
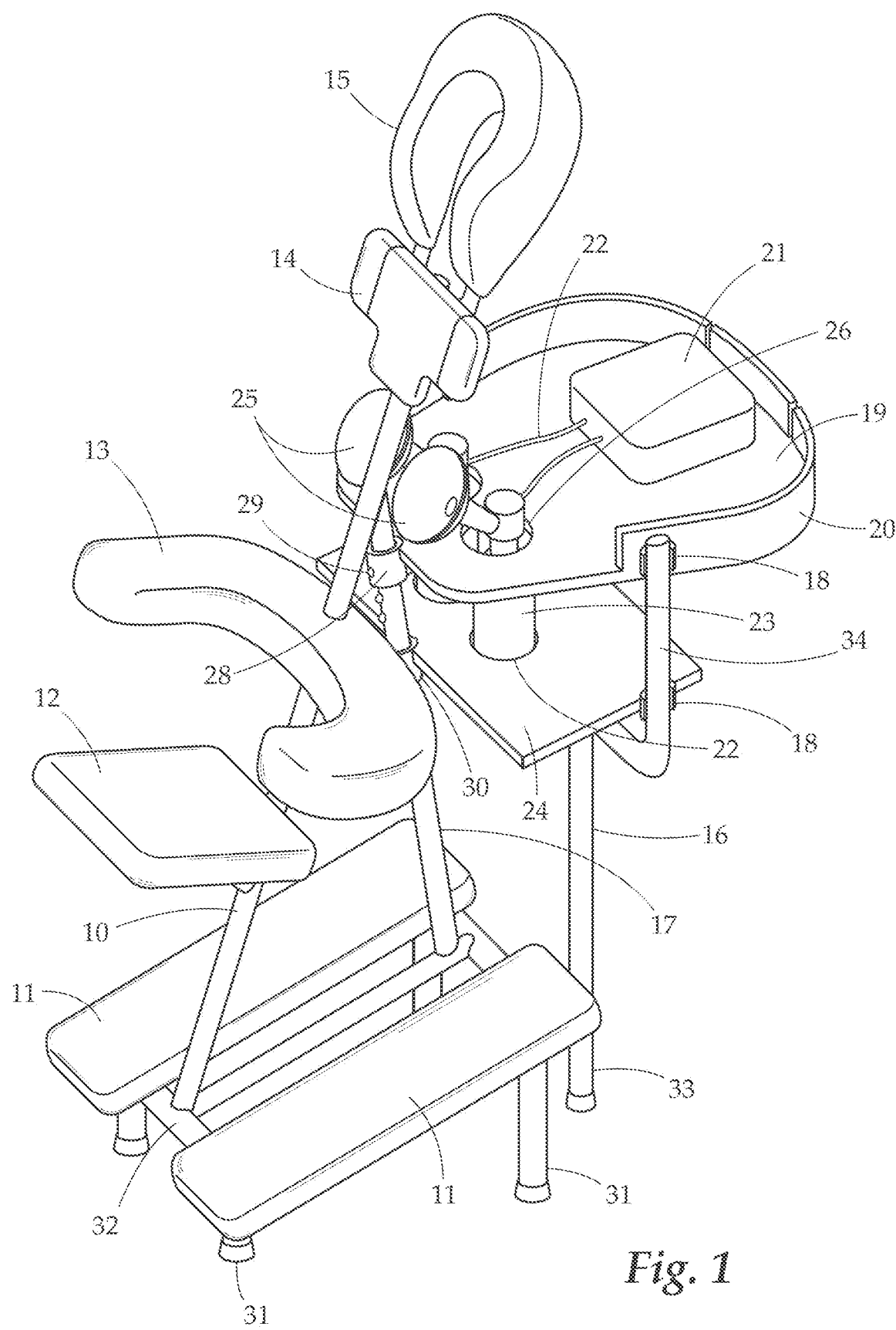
FIG. 1 provides a perspective view of an embodiment of a breast pumping chair.

The detailed description set forth below in connection with the appended drawings is intended as a description of presently preferred embodiments of the invention and does not represent the only forms in which the present disclosure may be constructed and/or utilized. The description sets forth the functions and the sequence of steps for constructing and operating the invention in connection with the illustrated embodiments.

Generally, the present disclosure concerns a breast pumping system which allows a mother who is pumping breast milk to rest in a comfortable and effective pumping position. The system involves a forward-leaning chair which angles the body forward, and allows the mother's front to rest on various supports. In a particular embodiment, the forward-leaning chair may be angled at 60 degrees from prone and/or 45 degrees from prone. A breast pump table is positioned ahead of the mother's breasts, which can be connected to bottles and a breast shield (also referred to as a funnel, or flange). The mother, once positioned on the chair, can connect the breast shields and activate the pump, allowing her to pump in an ideal position without holding the breast milk bottles with her hands. The breast pumping system disclosed utilizes gravity (by the forward-leaning) as well as optimal body positioning and comfort to allow for maximum pumping success.

The breast pumping system may be integrated with a forward-leaning chair, or may be formed as an add-on to existing forward-leaning chairs, such as a massage chair. In preferred embodiments, various components including the breast pump table, support pads, and the like, may be adjustable in position to accommodate for both different sized bodies, and also to accommodate for the change in an individual mother's postpartum body, which can change significantly. The bottles may also rotate clockwise or counterclockwise among other various directions and ranges of motion.

In one embodiment, a breast pump table may be positioned on the chair at approximately breast-level when a user is resting on the chair. This puts the breast pump in an easily accessible position for the mother. Various structures may be employed to aid in holding the breast shields, and bottles connected thereto, to the breasts. For example, the table and/or entire assembly may shift backwards and forwards as well as up and down, left and right relative to the chair to engage with the breast shields of the bottle with the breasts. This allows for hands-free operation, increasing relaxation and comfort. In one embodiment, the chair may have a breast holder formed as a panel with breast-sized openings. The breast shields, which seal to the breasts and funnel to the bottles, may seat in these openings, with the bottles on the opposite side of the panel. A user may lean forward such that the breasts engage with the breast shields, and as supported by the chair, is positioned in a relaxing and physiologically optimal position for pumping and breast milk expression. In many embodiments, the position and orientation of the breast holder panel with respect to the chair may be adjustable in numerous directions to optimize comfort to the user, and to adjust to the mother's changing post-partum body. Other solutions to hold the shields to the breasts may include a strap, special bra designed for such a use, securing the bottles in position, and the like.

In certain embodiments, depending on configuration, the breast pump table may include a bottle shelf which positions the pump above or below the bottles which rest on the shelf. In various configurations, this may yield a more accessible and comfortable experience for the user, making the pump and bottles more accessible and less prone to spillage and tipping. In certain embodiments, the breast pump table may have a perimeter ridge to contain spills and prevent accidental sliding off of the breast pump and optionally bottles placed thereon. In another embodiment, the bottle shelf may have a perimeter ridge. In yet another embodiment, the bottle shelf may have one or more holders to hold bottles in place securely.

In one embodiment of the forward-leaning breast pumping chair as a whole, typical components include a center post which angles forward from a base or feet. A seat is attached to the post and similarly angled forward, causing the user to be drawn towards the post by gravity to a forward leaning position. In some embodiments, a safety belt or similar strap may be included to hold the user to the seat, abdomen rest, or to another part of the chair and/or table. This provides added security in case the user falls asleep and generally encourages relaxation. A chest rest and optional shin rests are attached to the post to support legs and chests of the user. Further, a head rest is positioned on the post to allow a user to rest their head comfortably. The breast pumping chair may also include arm rests and an abdomen rest to increase comfort, and thus relaxation, for the breast-pumping user. In addition to these components, a table for holding the breast pump, and an optional breast holder for supporting and positioning the breasts may also be included on the chair, allowing a seated mother to easily pump breast milk by placing her breasts appropriately, and connecting to a pump, which may be resting conveniently on the table. In further embodiments, the table and/or breast holder may further be supported by a foldable arm which allows them to fold or pivot relative to the forward-leaning chair so as to move out of the way, to reduce space and improve access (sitting and standing) from the chair. In varying embodiments, the chair may be set at multiple supportive forward-leaning positions and in some embodiments may fold up for storage.

In some embodiments, an existing forward-leaning massage chair may be modified to have a breast pumping system including an attached breast pump table and/or a breast holder to support and position the breasts. The table and/or breast holder can be removably attached to the forward-leaning massage chair and once attached, may be adjustable in one or a plurality of axes. Connection may be achieved in any manner, including but not limited to snapping on, clamping, connectors, pins, bolts, screws, adhesives, and the like. In further embodiments, as noted above, the table and/or breast holder may further include a foldable arm which allows them to fold or pivot relative to the forward-leaning chair so as to move out of the way, to reduce space and improve access (sitting and standing) from the chair.

In many embodiments, the breast pumping system and its various embodiments herein may further include a carrying case. The carrying case may be sized to fit the breast pumping system, which may vary in size depending on if it is a chair, table, or tabletop embodiment to fit the breast pumping system. In addition to being sized to fit the breast pumping system, the carrying case may optionally include storage compartments for one or more of a breast pump, one or more bottles, an insulated storage space for an ice pack and to store pumped milk and/or frozen or chilled milk, and an added storage space for miscellaneous items.

Figure 2:
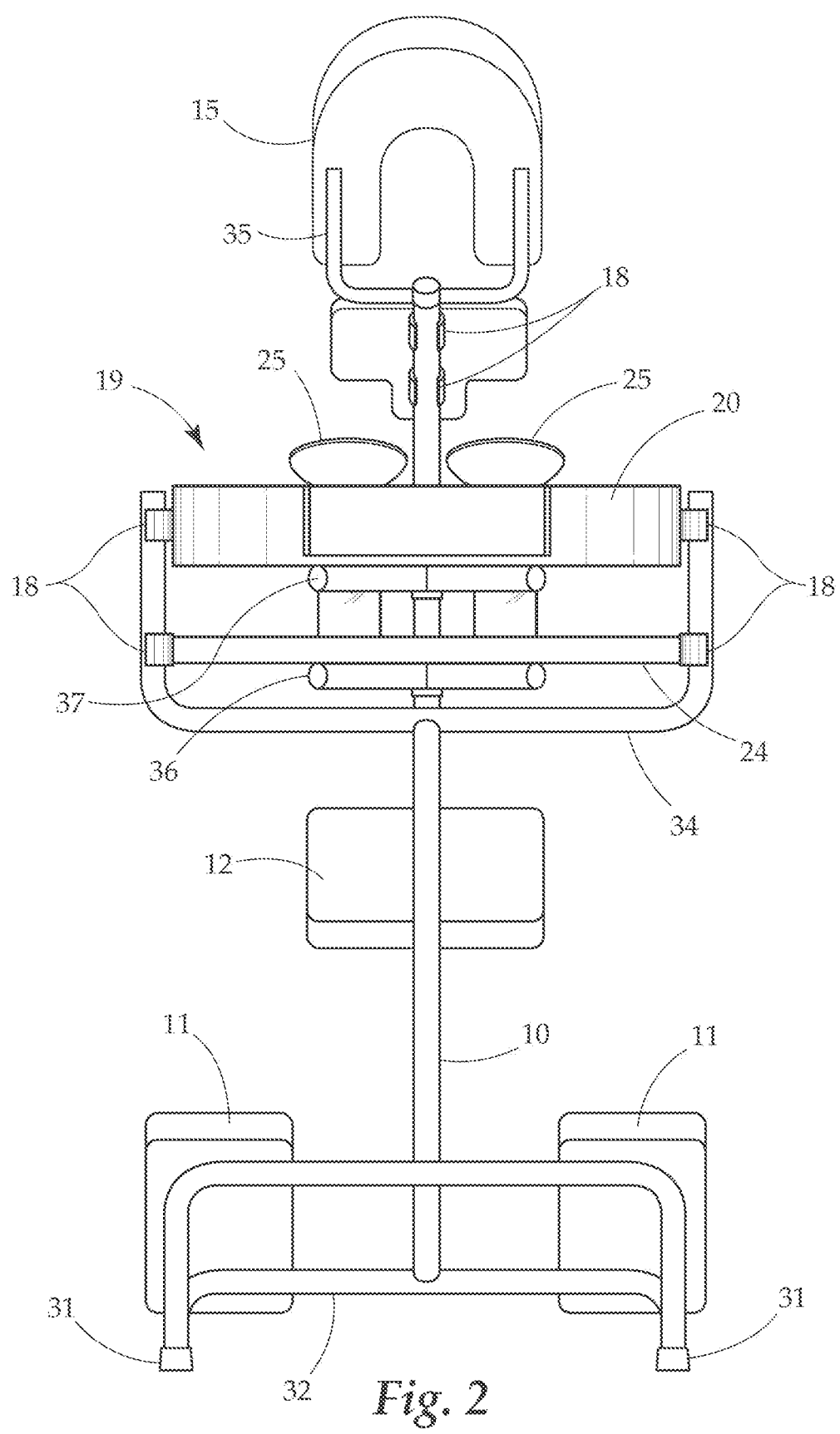
FIG. 2 provides a frontal view of the embodiment of FIG. 1.
Figure 5:
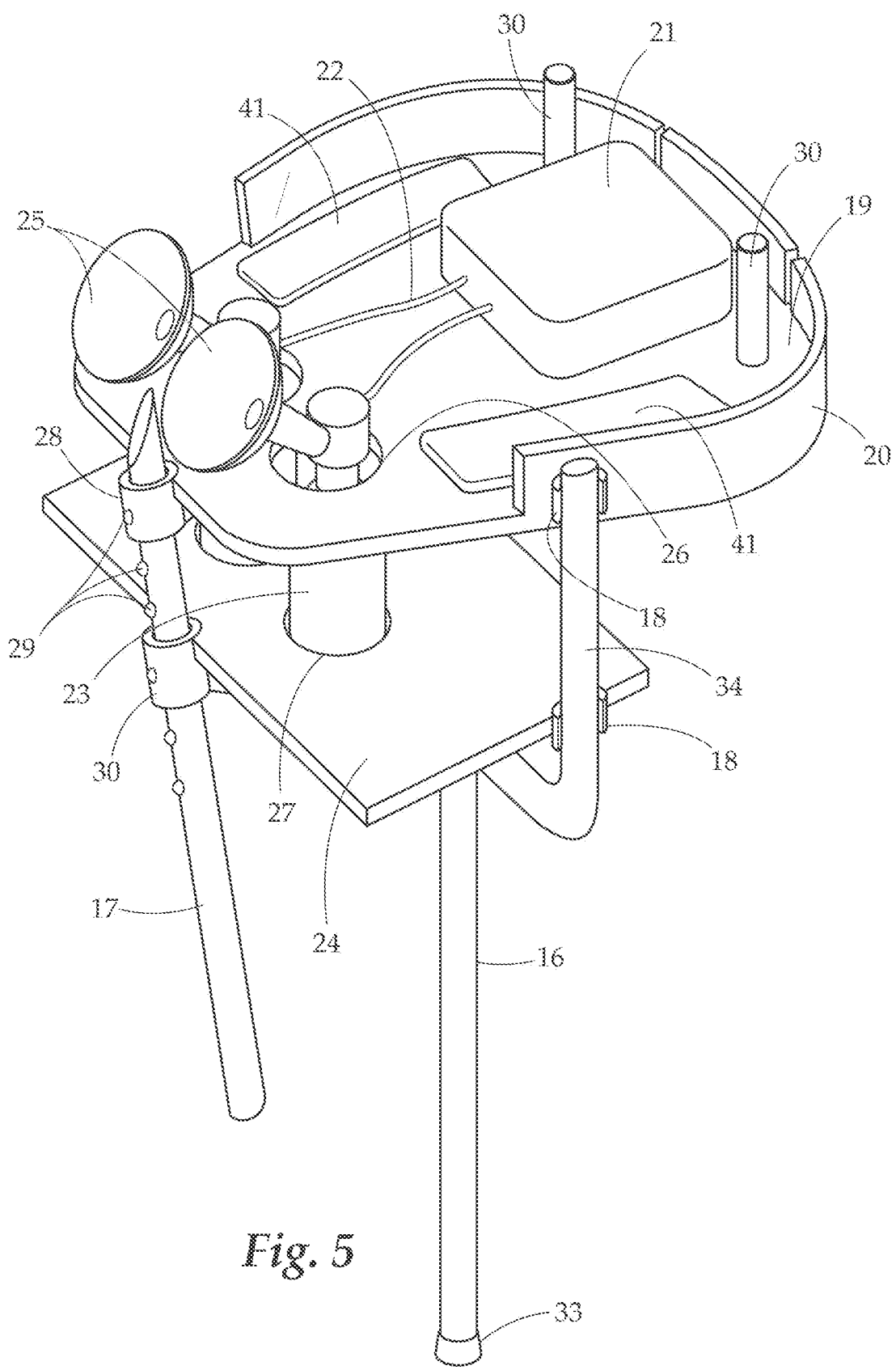
FIG. 5 provides a perspective view of an embodiment of breast pumping components of the breast pumping system.
Figure 10:
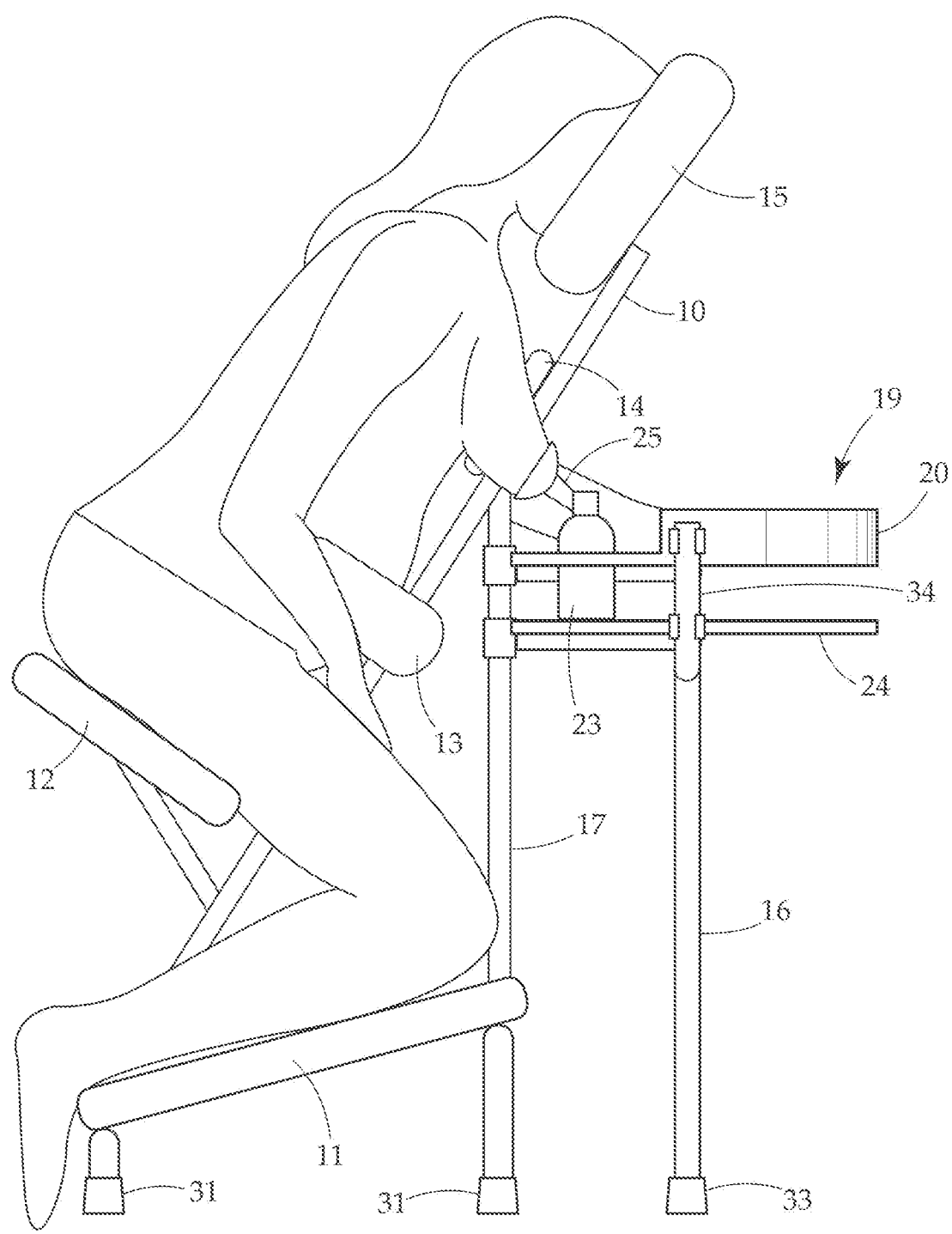
FIG. 10 provides a side view of an embodiment of the breast pumping system in use.

Turning now to FIGS. 1, 2, and 5, perspective and front views of an embodiment of the breast pumping system integrated into a forward-leaning chair is provided. The chair is based around a central post 10 which angles a seat 12 forward relative to a base 31, 32 resting on the floor. In certain embodiments the base 31 may have feet which are made to contact the floor. In other embodiments (not shown) the base 31 may have casters, allowing easy movement of the chair along the floor. Casters may be locked and/or retracted to safely hold the chair in place when being used. A seat 12, shin rests 11, abdomen support 13 with optional seatbelt, chest support 14, and head rest 15 all provide support to a person's body resting in the chair. These may each be adjustable in position and orientation in height, angle, and in some cases, lateral direction, in certain embodiments, so as to maximize comfort and relaxation to the user. In FIG. 10, the forward-leaning chair and breast pumping system can be seen in use by a user who is pumping breastmilk.

In this view, the breast pumping components are built in to the chair, although as noted above, the components may be removably attached in other embodiments. As shown in the embodiments of FIGS. 1, 2, 5, and 10, a support bar 17 extends from the base 31, 32 to the central post 10. A breast pump table 19 and bottle shelf 24 are connected to this bar 17 via connectors 28 and 30, which surround the bar 17 and are slideable along it. In this embodiment, the connectors 28, 30, and in turn the pump table 19 and bottle shelf 24, can be secured in place by pins 29 passing through an aperture in each connector 28, 30. Adjustment is achieved by pressing on pin 29 so that it does not extend through the aperture, and then sliding connectors 28, 30 along support bar 17. Other adjustment, such as distance from center post 10 may be possible as well via, for example, a telescoping shaft (not shown). Of course, other structures for holding the connectors in place to the bar 17 may be used without straying from the scope of this invention.

The breast pumping components are supported by a support 16 having a foot 33 resting on the ground. In other embodiments, a caster or casters may replace foot 33. In another embodiment, the breast pumping shelf 24 and table 19 may be supported by one or more support 16 legs having casters at their end, so that the shelf 24 and table 19 can be easily moved around a floor by the casters (not shown). In other embodiments, connection to the center post 10, whether directly or indirectly, and permanently or removably, may be sufficient to support the breast pumping components. Bottle shelf 24 connects to an upright 34, supported by cross bar 34, via clip 18. The bottle shelf 24 in this embodiment also includes a bottle holder 22 formed here as a recess in the surface of the bottle shelf 24. In operation, the bottle 23 can sit into the bottle holder 22 recess to increase stability and limit accidental spillage of the bottle or disconnection of the shield 25 from a breast.

Breast pump table 19 is designed to hold a breast pump and also in most embodiments, to provide convenient placement of breast pumping shields 25 which are connected to bottles 23. An angle, height, position, and direction of the breast pump table 19 can be adjusted for maximum comfort. In one embodiment, a ball and socket joint may be used to connect various components to allow for multi-directional adjustment. In the embodiment shown, the breast pump table 19 comprises a perimeter ridge 20 which operates to prevent items from sliding off the table 19, and optionally to contain any spills. Further, openings 26 allow bottles held on the bottle shelf 22 below to pass through. In other embodiments (not shown) bottles 23 may rest on the breast pump table 19 instead of on a different shelf. Breast pump 21 rests on the breast pump table 19, in most embodiments, the breast pump 21 has tubes 22 drawing a low pressure connected to the shields 25, which cause the pumping action. While shown permanently connected to the elements of the chair, it should be understood that in other embodiments, the breast pumping components (table 19, shelf 24) may be removably connected to the chair, and in further embodiments may be movable relative to the chair while connected.

Bars 37 and 36 are used in this embodiment to support breast pump table 19 and bottle shelf 24, respectively. These bars connect to the connectors 28, 30 to provide strength to the table 19 and shelf 24. Head rest 15, in this embodiment, is connected to an end of the center post 10 by a support bar 35. As assembled, the breast pumping chair and components allows for a mother to be optimally positioned to maximize pumping effectiveness by facing forward causing gravity to assist in milk expression, and to be in a very comfortable and relaxed position, reducing stress and relaxing the body leading to improved milk expression.

Figure 3:
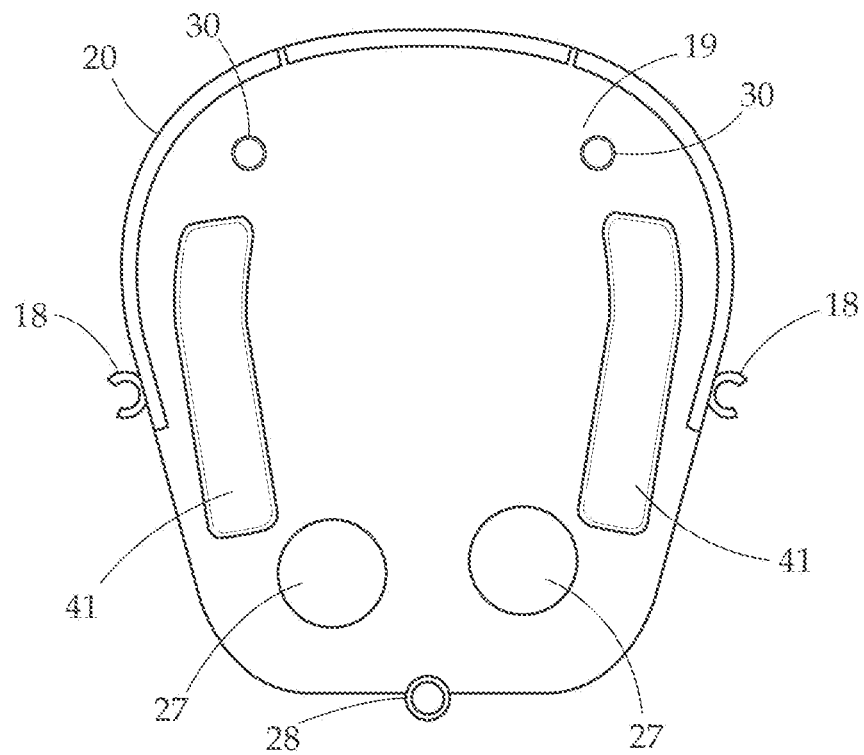
FIG. 3 provides a top view of a breast pumping table attachable to a forward-leaning chair.
Figure 4:
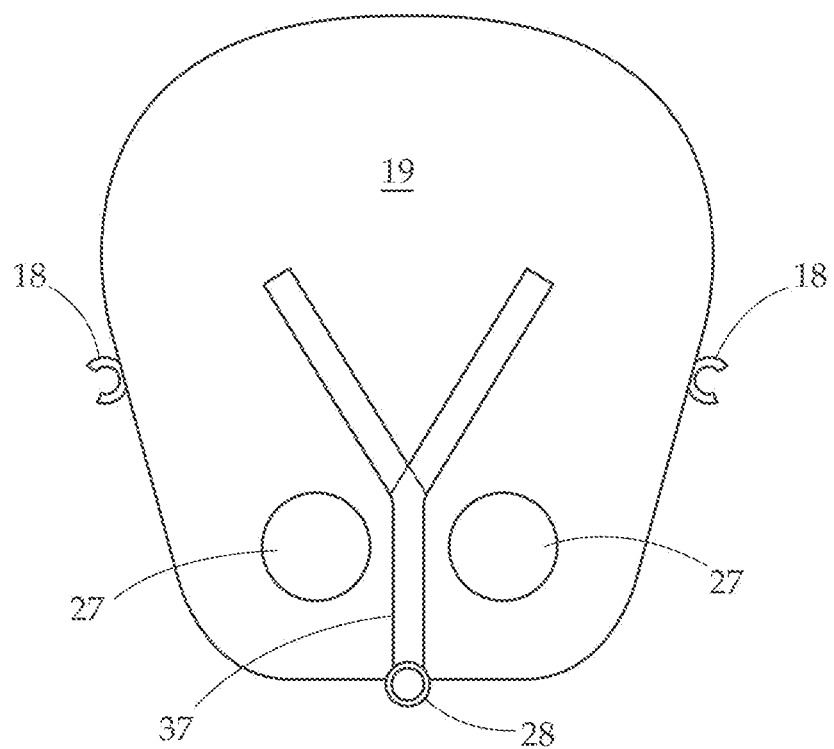
FIG. 4 provides a bottom view of a breast pumping table attachable to a forward-leaning chair.

FIGS. 3 and 4 provide a view of an embodiment of the breast pumping table which may be removably or permanently attached to the forward-leaning chair. Table 19 has ridge 20 around its perimeter. Clips 18 allow, in this embodiment, connection to uprights of the breast pump component assembly. Of course, other modes of connection, whether permanent or removable are within the scope of this disclosure. In this view, the table 19 includes arm rests 41, which provide a padded and/or contoured area for a user to rest their arms. Table 19 also includes handles 30 for a user to hold onto, providing comfort and allowing a user to adjust body position and/or shield 25 position by pulling and otherwise manipulating the handles. Openings 26 allow the bottle and/or shields or parts thereof to pass through the table 19. Connector ring 28 allows connection to a support such as bar 17. As with clips 18, any structure may be used to permanently or removably connect the table 19 to the forward-leaning chair. In this view, a 'Y' shaped bar 37 connects to connector and supports the table 19. A handle (not shown) may be positioned anywhere on the breast pumping table 19 and/or on the bottle shelf 24 to aid in movement of the table as well as the entire chair assembly. Further, table 19 and shelf 24, in certain embodiments, may have a pivotal connection allowing them to fold upward or downward into a compacted position. This hinged connection may be at the connector ring 28, or the table 19 and shelf 24 may be hingedly connected to the chair at, for example, center post 10.

Figure 6:
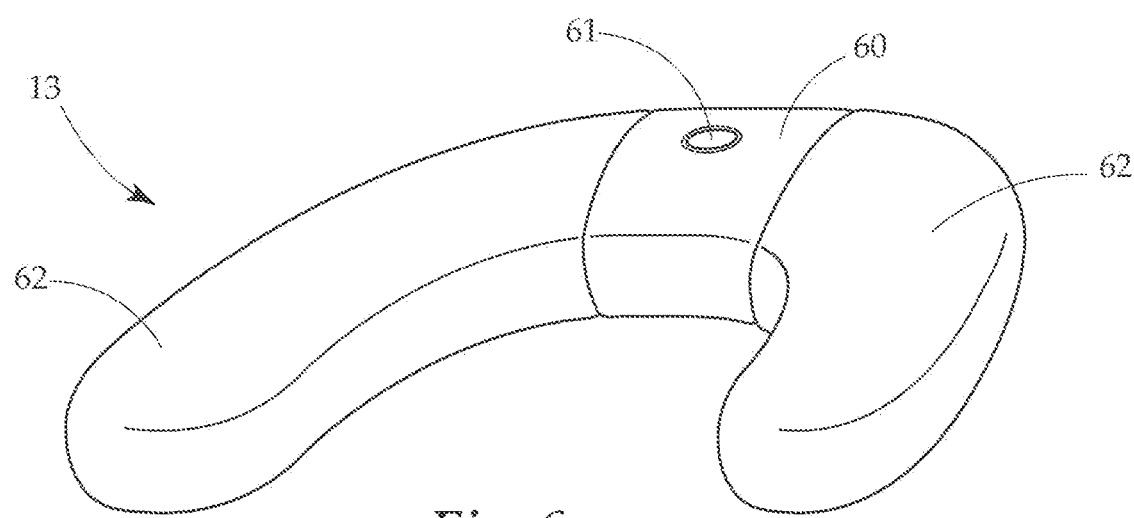
FIG. 6 provides a perspective view of an embodiment of an abdomen rest for the forward-leaning chair.
Figure 7:
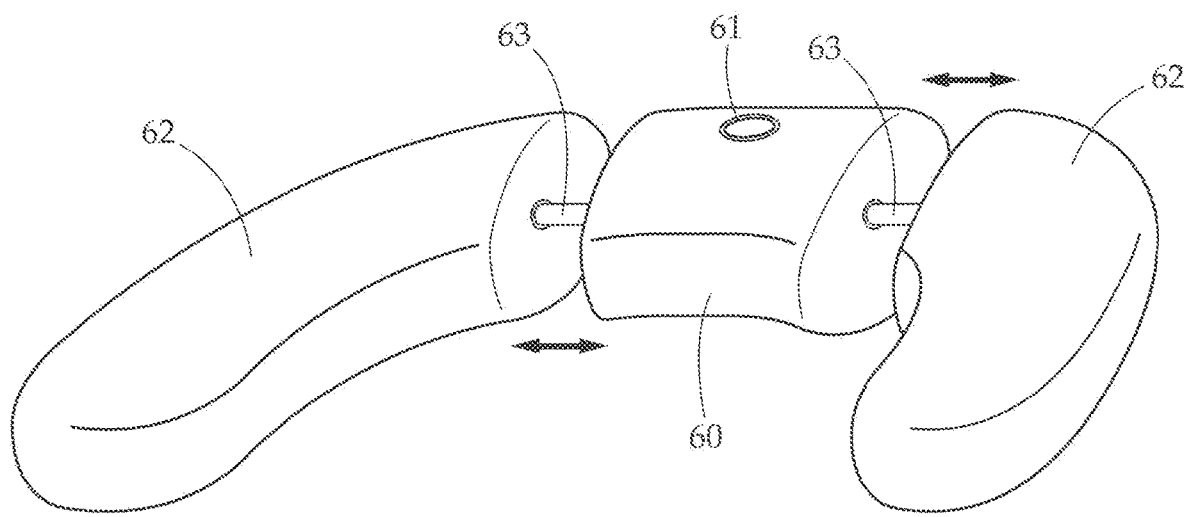
FIG. 7 provides a perspective view of an embodiment of an abdomen rest for the forward-leaning chair.

FIGS. 6 and 7 show an embodiment of the abdomen rest of the forward-leaning chair. In this embodiment, abdomen rest 13 has a base 60 and arms 62 which are shaped to wrap around an abdomen of a user. In certain embodiments, the abdomen rest may be padded and in some embodiments may have a seatbelt. The base 60 has an opening 61 through which a center post may pass. Other modes of connection of the base 60 to the forward-leaning chair may also be employed, such as a clip, clamp, or permanent welded or molded connection, among others. As shown in FIG. 7, the arms 62 of the abdomen rest 13 are adjustable in position. Arms 62 connect to shaft 63 which can allow the arms to extend outwardly and to optionally rotate about an axis of the shaft 63. This allows the abdomen rest 13 to be maximally adaptable for varying sized mothers.

Figure 8:
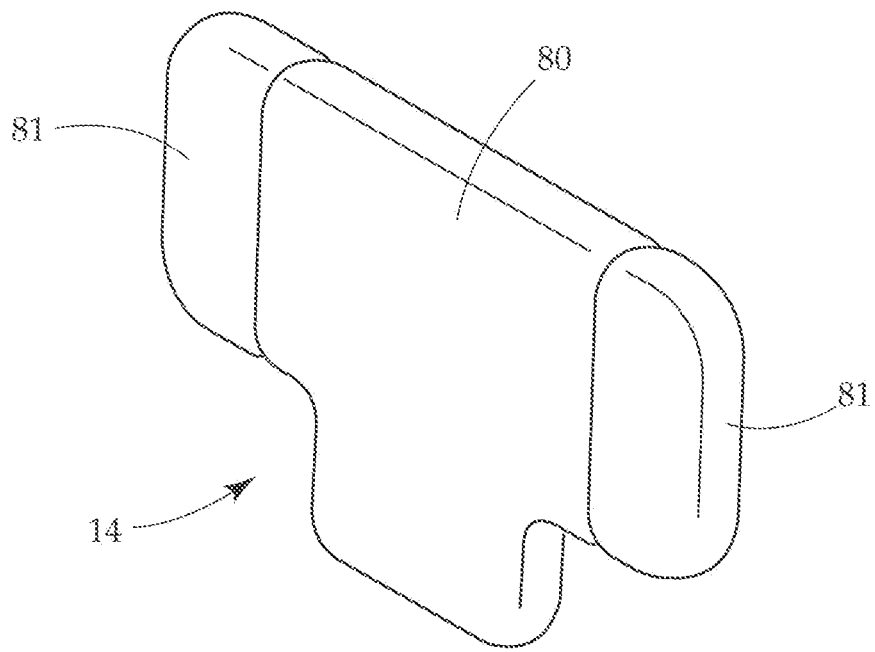
FIG. 8 provides a perspective view of an embodiment of a chest rest for the forward-leaning chair.
Figure 9:
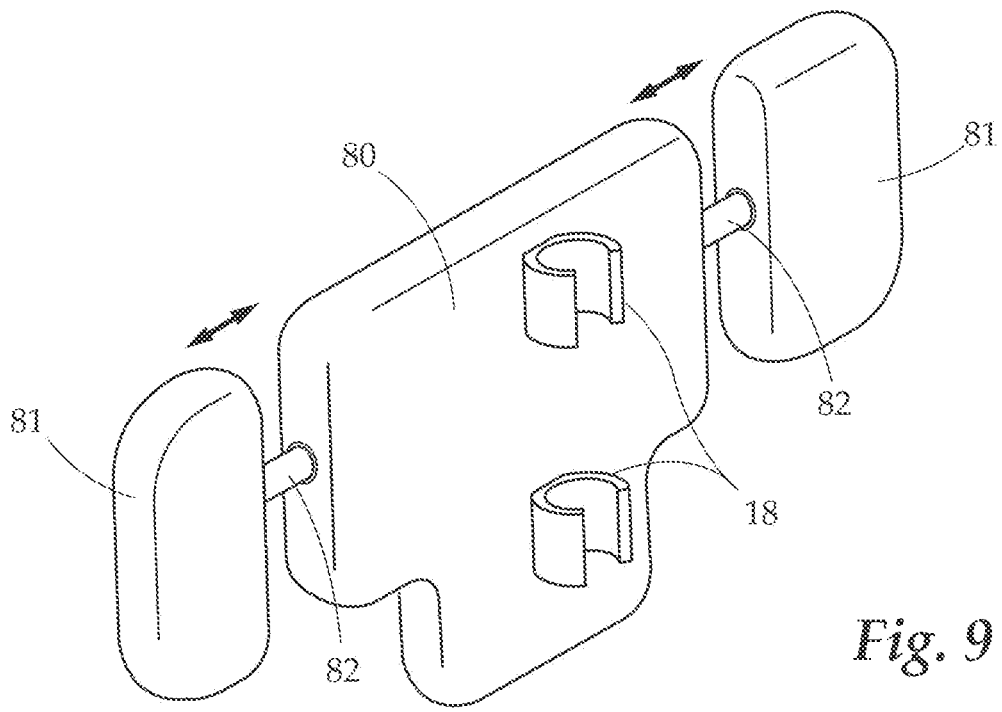
FIG. 9 provides a perspective view of an embodiment of a chest rest for the forward-leaning chair.

FIGS. 8 and 9 show an embodiment of a chest rest of the forward-leaning chair. The chest rest 14 has a base 80 which can be connected to the forward-leaning chair, as well as arms 81 extending from opposite sides of the base 80. On the rear of the base, in this embodiment, are two clips 18 which may removably and adjustably attach to a center post of the chair. Other modes of connection of the base 80 to the forward-leaning chair may also be employed, such as a hole through the base 80, clamp, or permanent welded or molded connection, among others. As shown in FIG. 9, the arms 81 of the chest rest 14 are adjustable. Arms 81 connect to shaft 82 which can allow the arms 81 to extend outwardly and to optionally rotate about an axis of the shaft 63. This allows the chest rest 14 to be maximally adaptable for varying sized mothers. Other elements of the chair may have structure like this to allow them to be similarly adjustable.

Figure 11:
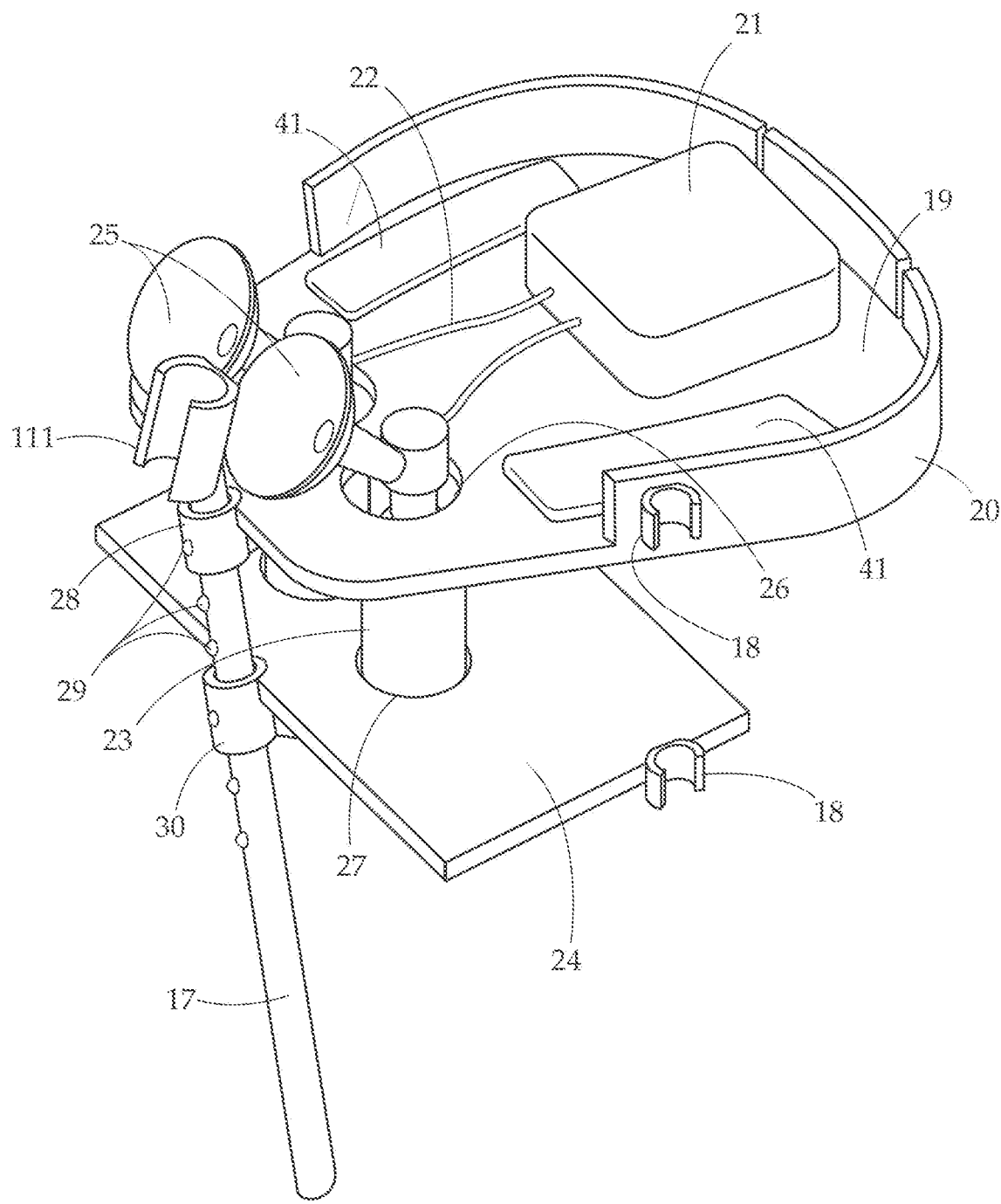
FIG. 11 provides a perspective view of breast pumping components of the breast pumping system.

FIG. 11 provides a view of a removable embodiment of the breast pumping system, which may be attachable to an existing forward-leaning chair such as a massage chair. Here, the previously described components including the breast pumping table 19 and bottle shelf 24 below are connected to a support 17. The support 17 is shown here as a bar which allows for relative movement along the bar of the table 19 and shelf 24. This bar 17 may connect to a forward-leaning chair such as a massage chair, or may be free at its end without connection. In certain embodiments, bar 17 may removably connect to the forward leaning chair by, for example, clipping into the base, having a foot which rests on the base, a frictional connection to the base, and the like. However, in other embodiments, any sort of support may be used without straying from the scope of the invention. Notably, a connector, shown here as a robust clip 111 allows connection between the breast pumping system to the forward-leaning chair. In different embodiments, an optional support leg, such as leg 16 as shown in other figures, may also be attached to the shelf 24 and table 19 to provide additional support. As such, an existing forward-leaning chair may be used as a breast pumping chair system allowing a user to rest on the forward-leaning chair and comfortably pump breast milk.

Figure 12:
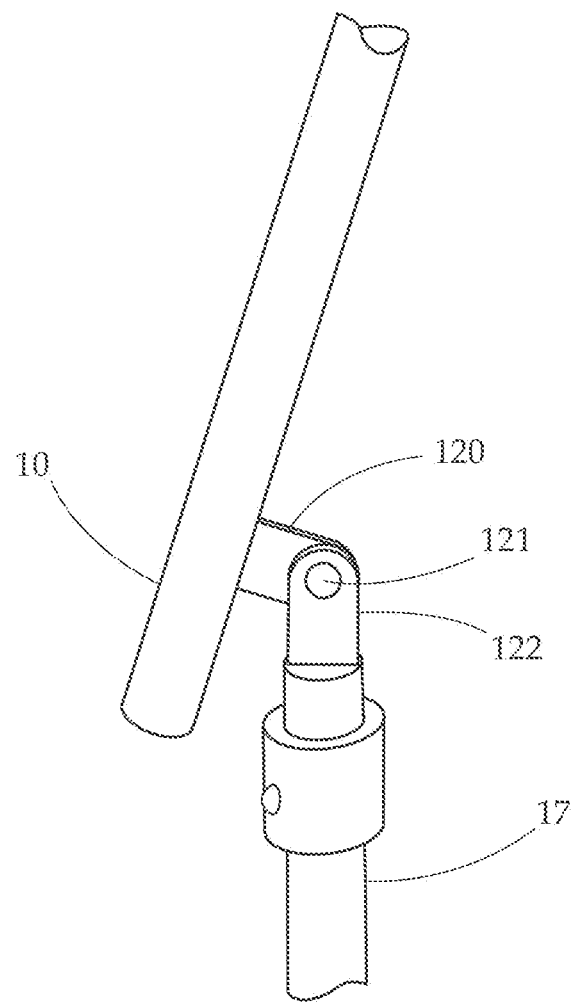
FIG. 12 provides a detail view of components of the breast pumping system.

FIG. 12 provides a view of a hinged connection between the center post 10 and support 17. In such an embodiment, the hinged connection allows for adjustment of the breast pumping table 19 and/or shelf 24, and thus adjustments of any components thereon. This may be particularly advantageous to bring the breast shields 25 in optimal position relative to the breasts of the breast pumping mother to achieve a good seal and thus effective pumping. In this view, two stems 120, 122 extend from the center post 10 and the support 17, respectively. These stems 120, 122 are pivotally movable about hinge 121. In a related embodiment, Stem 120 may be joined to a connector (not shown) such as clip 111 of FIG. 11, to allow for removable connection of the breast pumping system to a forward-leaning chair.

Figure 13:
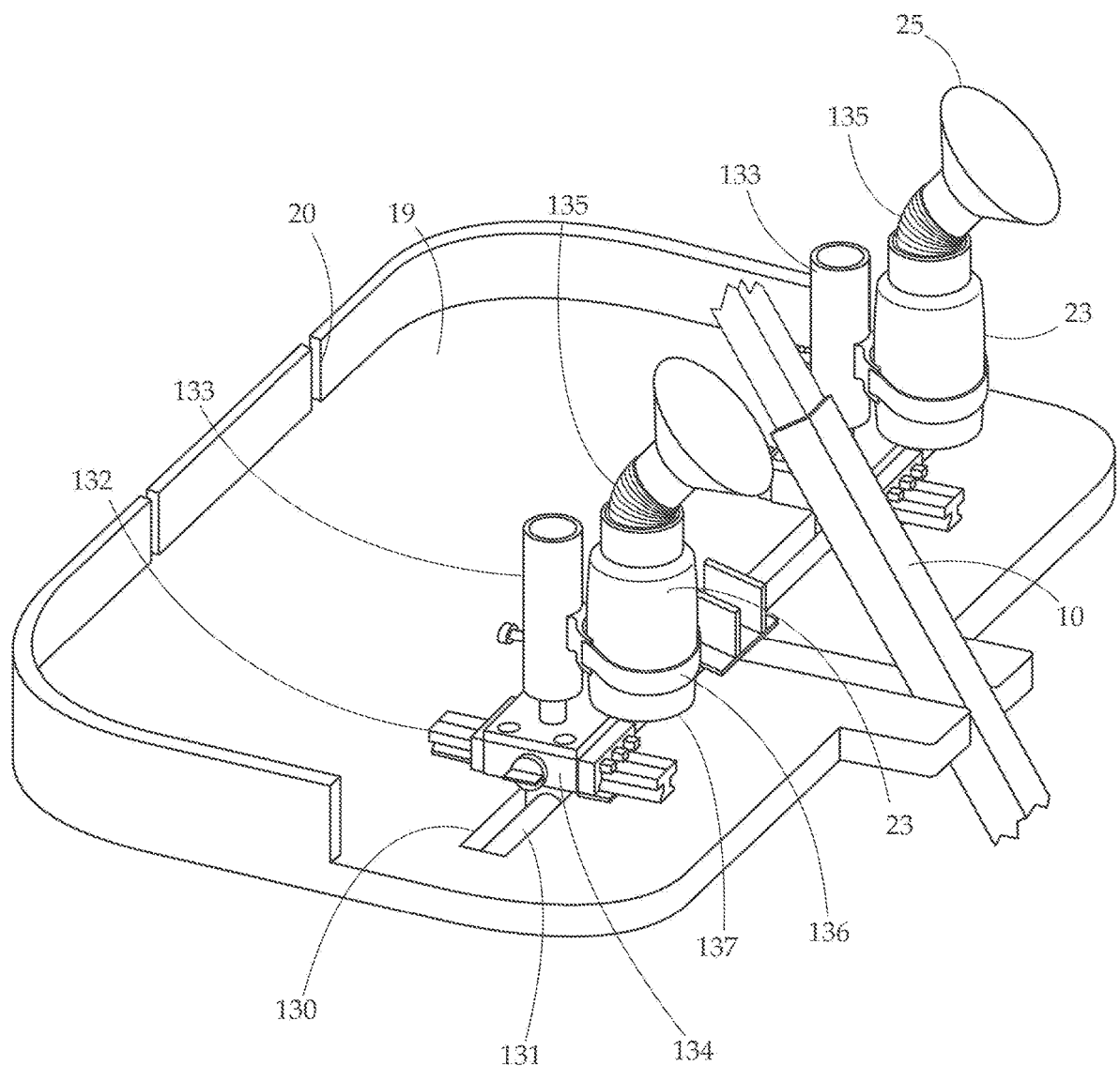
FIG. 13 provides a view of another embodiment of the table of the breast pumping system.

FIG. 13 provides a detail view of another embodiment of the table of the breast pumping system. In this view, the bottles 23 are connected to the table by way of a multi-directional adjustable bottle holder base assembly. The adjustable base assembly is formed of a base 134 which can move left to right, forward and back along a horizontal plane. The base 134 connects to the table 19 at a slide bar 131 which is set into a channel 130 of the table 19. Of course, other slideable or adjustable configurations may be used without straying from the scope of this invention. Further, the base 134 is also slidably mounted to a distance slide bar 132, which allows for adjustment of the base location forward or backward relative to a front or rear edge of the table. Extending upward from the base 134 is a bottle holder column 133. The column 133 is pivotally connected to the base 134 so that it can rotate about its major axis, which in turn allows the bottle 23 attached thereto to pivot. Other configurations other than a column may of course be used to connect the bottle 23 to the base 134. A bottle holder 137 is connected to the column 133. The bottle holder may be any structure which allows the bottle to be held in place. In this embodiment, the bottle holder 137 has a base on which the bottle 23 rests, and a strap 136 which holds the bottle tightly in place. A clamp holds the bottle holder 137 to the column 133. This clamp can be loosened to move the bottle holder 137 upwards and downwards. As with the other components, the bottle may be held by various structures which allow upward and downward movement and connection to the column 133 without straying from the scope of this invention. The breast pump table 19 further comprises a perimeter ridge 20 which operates to prevent items from sliding off the table 19, and optionally to contain any spills. In the view shown, two slits are present on the ridge which allow passage of cords such as power cords for the breast pump. These ridges may extend all or part of the height of the ridge. In some embodiments, the adjustable bottle holder base assembly may be removable from the table 19 and may act as a stand-alone bottle holder which can be positioned on or connected to any surface or material, allowing for portable and comfortable breast pumping.

Figure 14:
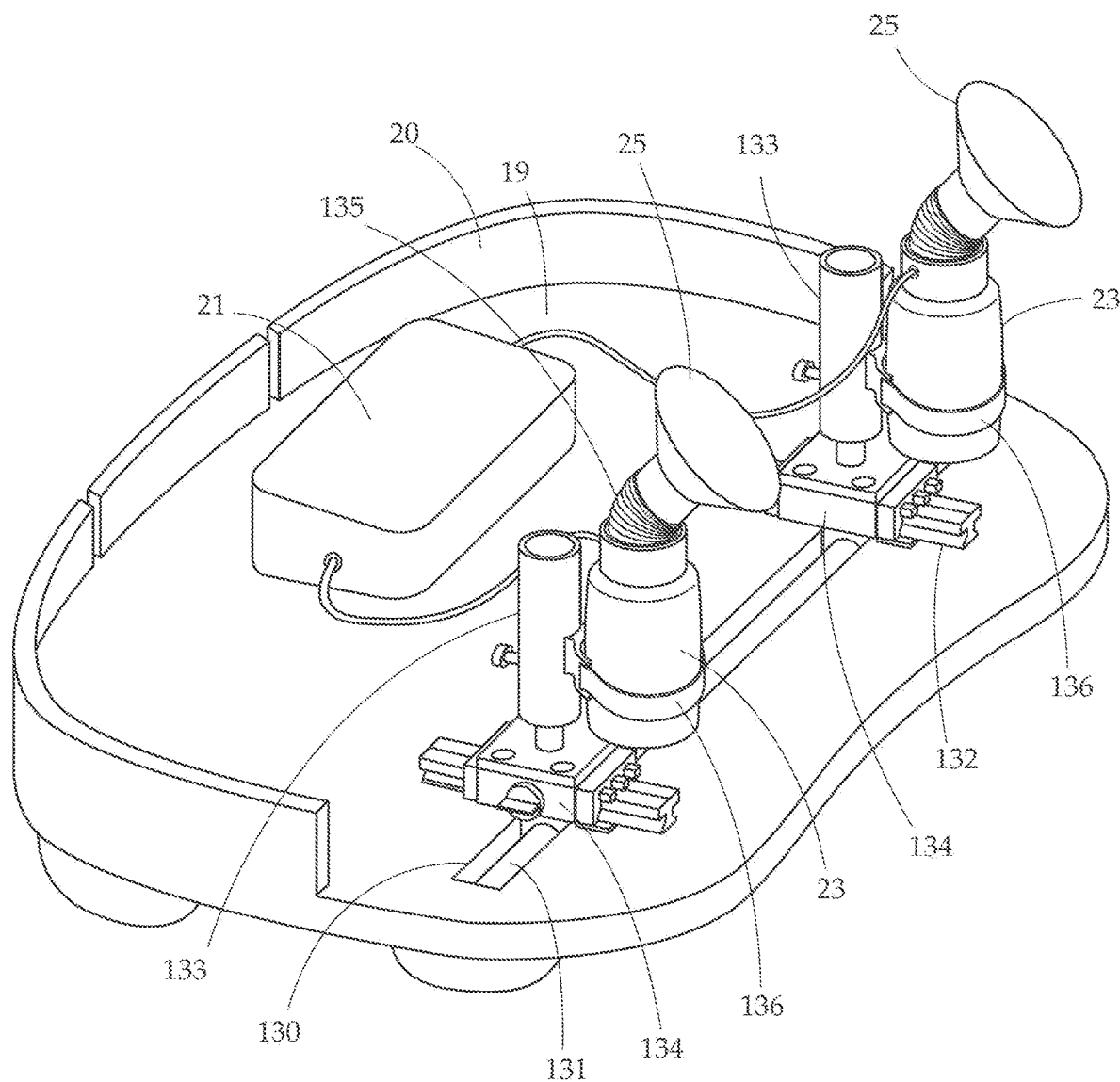
FIG. 14 provides a view of yet another embodiment of the table of the breast pumping system.

FIG. 14 provides a view of an embodiment of the breast pumping table which is separate from the chair. This view contemplates a stand-alone table platform on which a breast pump 21 and bottles 23 may rest. This allows for a breast pumping mother to comfortably relax while pumping, rather than having to uncomfortably hold the bottles and have to activate/operate the pump. Also, the headrest is completely removable to create a hands-free workstation. The table 19 allows for a laptop, tablet, or other electronic device to rest on the table with the pump. In the particular view shown, the table 19 is formed as a platform or surface which can rest on a user's lap. In other embodiments, the table 19 may have foldable or telescoping legs to allow for lap and/or table leg-supported operation. A movable assembly for the bottles is shown integrated into the table 19, as in FIG. 13. However, this is not necessarily required for the stand-alone table embodiments. In lap based embodiments, pads or other structures may be used to elevate the table and make it comfortable. Similar embodiment may have rubber spacers, feet, pads, or a flat surface that can be placed on an approximately flat surface such as a countertop, kitchen island overhang, lap, table, desk, bedside stand, dresser, and the like. As noted herein, pumping effectiveness is greatly increased by optimizing body positioning, relaxation, and comfort. Accordingly, various improvements and features all aim to improve this body position optimization and relaxation. In certain embodiment, the table may incorporate a head rest (not shown) similar to that of FIG. 15.

Figure 15:
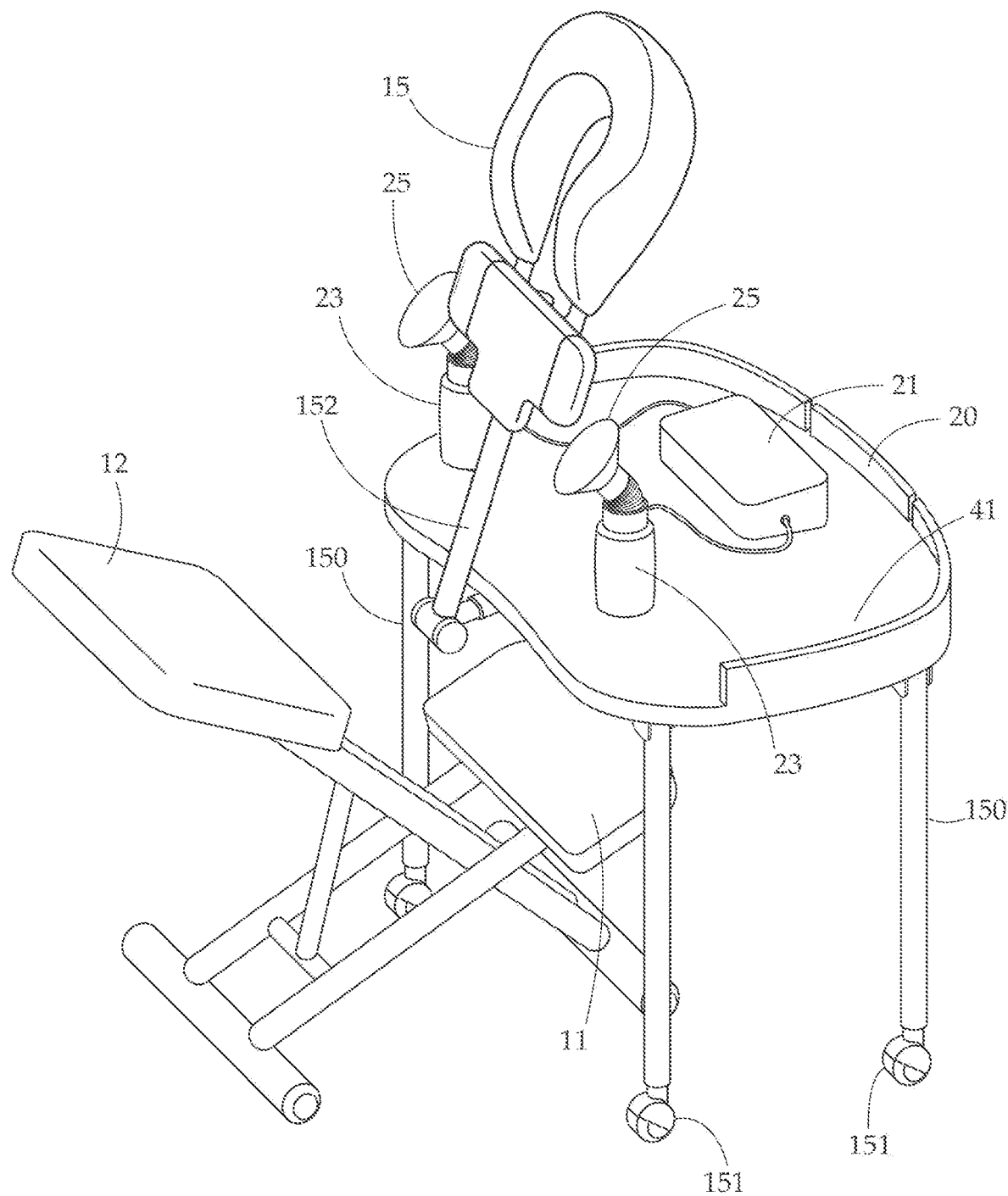
FIG. 15 provides a view of still another embodiment of the table of the breast pumping system.

FIG. 15 shows another embodiment of a stand-alone pumping table which holds the breast pump 21 and bottles 23. Similarly to the embodiment of FIG. 14, in this view, the table 19 supports the breast pump 21 and bottles 23 and provides an optimal positioning of the components for effective pumping. The table 19 further has a head rest 15 which extends from a top or bottom surface, or side. The head rest 15, in many embodiments, is removable both in the embodiment of FIG. 15 as well as all other embodiments disclosed herein. In this embodiment, a shaft 152 provides a hinged connection to the table. As such, the head rest 15 can be adjusted in position, and can also be folded away for compact storage of the table. Or course, any connection structure may be used to connect the head rest to the table. The head rest 15 being connected to the table 19 may be applied to any of the other embodiments disclosed herein, such as that of FIG. 14 among others. This view of the table shows a forward leaning chair having a forward-angled seat and a shin or knee rest 11, allowing the pumping user to comfortably lean forward during the pumping. However, it should be understood that any chair or other seating arrangement, a standing forward-leaning configuration, a lying prone position, kneeling, leaning forward on a pad, and the like, may be used without straying from the scope of the invention. Legs 150 extend from the bottom of the table 19. Ends of some or all of the legs 150 may have lockable casters 151 to facilitate movement of the table. In certain embodiments, the legs may be adjustable in length to change a height of the table. Further, the legs 150 may be hingedly connected to the table, to allow them to fold up for convenient storage, transportation, and optional lap use. In a further embodiment, the legs may be telescoping to adjust in length. In a particular embodiment, legs may vary from 12-48 inches in length, but of course other leg lengths are within the scope of this disclosure. In some embodiments, a water bottle holder may be connected to the table 19 so that the pumping woman can stay hydrated. Also, pads may be positioned on the table to provide a place to rest one's arms. These pads may be proximal to the pumping woman extending across the width of the table 19, or may extend along the sides of the table 19, or both.

Figure 16:
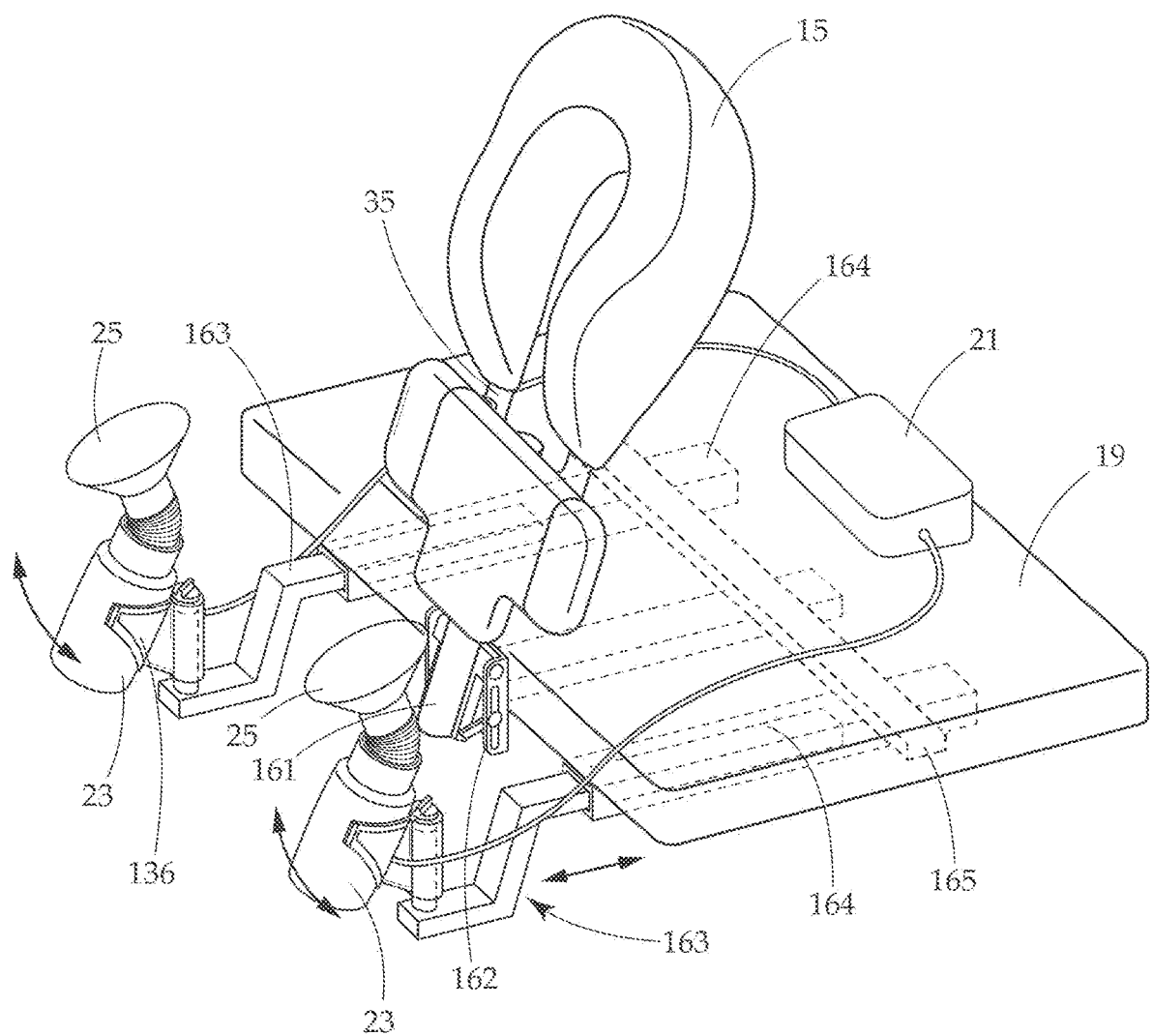
FIG. 16 provides a view of an embodiment of the table of the breast pumping system.

FIG. 16 shows yet another embodiment of the breast pumping system contemplated herein. This embodiment provides a breast pumping table and system which can be placed on, fastened to, and locked in place on a table, countertop, overhang, desk, and other similar flat surface. This configuration allows a nursing mother to lean forward in a resting position in front of a counter, seated at an existing table, in a person's lap, or the like. This allows for the hands-free pumping of breast milk in a comfortable, ergonomically supportive, forward leaning position to allow more milk to be expressed and prevent discomfort and injury from awkward pumping positions. This embodiment is similar to that of the breast pumping table disclosed above, but does not have legs on the table, allowing it to be placed on another flat surface, or approximately flat surface. The embodiment also has a different adjustable mechanism to allow for proper and comfortable positioning of the breast shields 25 for pumping breast milk. In some embodiments, legs may also depend from this pumping system configuration to support it up off the ground or other surface.

In the embodiment shown, the breast pumping table 19 has a headrest 15 extending from its top surface. The headrest 15 is connected to a shaft 161 which is hingedly connected to the table 19 via hinge 162. A bracket 35 connects the headrest to the shaft 161. In some embodiments, the headrest 15 and/or components such as shaft 161 and hinge 162 may be disconnected from the table 19 for portability and modular operation. In other embodiments, the headrest 15 and components are fixedly connected to the table, but can fold down into a compact position. Other embodiments include a combination of the two functionalities. Proper positioning of the shields 25 of the bottles 23 to receive pumped milk is very important for effective pumping and ergonomic pumping. In this embodiment, the bottles 23 and shields are adjustable by movement of a connecting shaft 163 which connects bottles 23 to table 19. Of course, other structures allowing for adjustable and secure bottle placement may be used without straying from the scope of this disclosure. A breast pump 21 is positioned on the table and in communication with the bottle shields 25.

The shaft 163 connects to bottles 23 at its distal end, and to the table 19 at its proximal end via a receiver slot 164. The receiver slot 163 is sized to have an opening into which shaft 163 can slideably fit into. Adjustment of the bottles 23 towards and away from the table is achieved by a movement of the shaft 163 into and out of the receiver slot 164. Of course, once adjusted, it is important that the shaft 163 and in turn bottles 23 say secured in position during the pumping operation so that the nursing mother can pump in a relaxed, hands-free ergonomically sound manner. Thus, a clamp, friction fit, piston control, threaded adjustment, and the like may be used to selectively secure the shaft 163 laterally in position relative to the receiver slot 164.

The bottle 23 is adjustable and rotatable in its connection to shaft 163. As shown by the arrows in FIG. 16, bottle 23 is adjustable relative to the shaft 163 in a pivoting motion by way of its rotatable connection to a bottle holder on the shaft 163. In this view, bottle holder allows the bottle to be angled upward for pumping. In still other embodiment, the bottle may be movable in an angled up/down motion via, for example, a hinge, flexing arm, and the like (not shown). In the embodiment shown, the bottle holder may be angled to orient the bottles at an upward angle to face a breast when the nursing woman is in a more leaning forward dangle pumping position. Further, in the embodiment shown, the receiver slots 164 themselves are movable towards or away from each other along a support cross bar 165. Movement in this direction is also selectively controllable and securable in position by, for example, clamp, friction fit, piston control, threaded adjustment, and the like. The breast pumping system as shown can be attached to or placed on a countertop, table, lap, and other flat or approximately flat surface to provide for a comfortable, secure, ergonomic and efficient pumping experience for a nursing mother.

Figure 17:
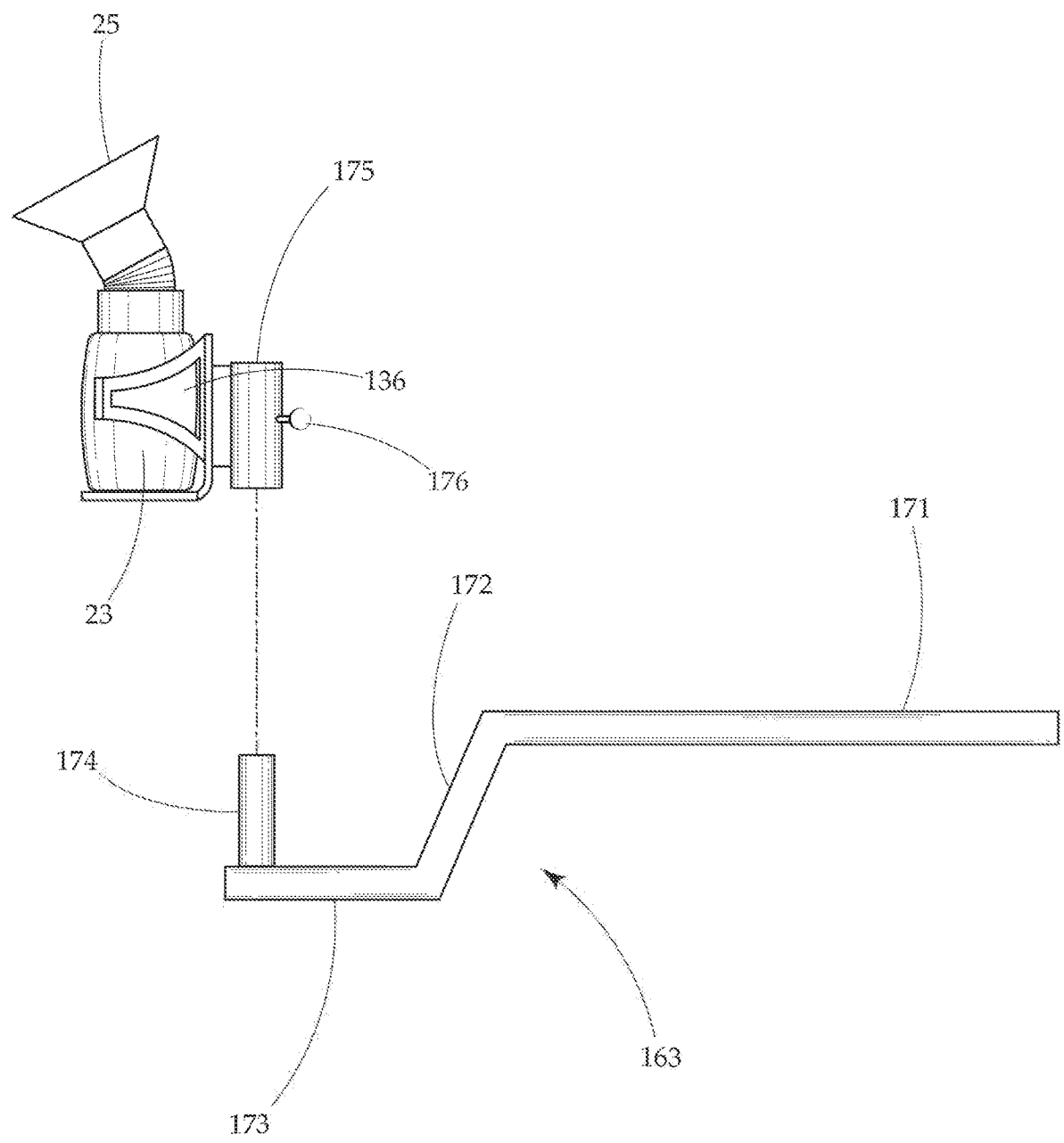
FIG. 17 provides a view of an embodiment of an adjustable shaft of a table of the breast pumping system.

FIG. 17 provides a detail view of an embodiment of the shaft which connects the bottle for receiving pumped milk to the table which holds the breast pump. The shaft 163 has an elongated portion at its proximal end which connects to the receiver slot and allows a sliding movement of the shaft therein. In many embodiments, shaft 163 and the bottle holding unit as a whole can be removed from the table 19. The elongated portion 171 is straight to allow for adjustment of distance from the table by sliding in and out of the receiver slot 164 and locking into place by the user to ensure proper bottle section and comfort while pumping breast milk. The shaft 163 has a downward angled portion at its middle. This shaping accommodates for a height of the bottle 23 and shield 25, such that the bottles can be placed on a surface that is lower than a surface on which the table rests. This allows for a more appropriate positioning of the bottle for connection to a breast while a woman is seated or standing near a flat surface. The shaft 163 has an extender 173 which joins to an upright post 174. The post 174 can be upright, or angled towards or away from the extender 173 to angle the bottle 23 and shield 25. A post receiver bracket 175 can fit over the post 174 and can rotate about a major axis of the post. This allows the bottle 23 to be pivotally connected to the shaft 163. The bracket 175, in many embodiments, fits over the post 174 in a tight frictional connection allowing pivoting motion against a slight frictional force. In certain embodiments, a thumb screw 176 or similar structure may be used to lock the bracket 175 to the post 174. Locking or securely holding the bottle in place maximizes user comfort and ensures proper positioning for pumping. The bracket 175 operates as a bottle holder by having a clip 136, which may also be a strap, arms, or the like to receive the bottle in a secure position. In some embodiments, the bracket 175 may also provide a base which extends from its bottom for the bottle 23 to rest on. As shown in this view, the post 174 is approximately vertical and can be fitted within bracket 175 which also is vertical, as well as the bottle holder clip 136 which holds bottle 23 vertically. In a slightly different embodiment shown in FIG. 16, the vertical post 174 and bracket 175 may correspond to an angled bottle holder which angles bottle 23 and in turn the breast pumping shield 25 upward. This angled configuration may allow the nursing mother to pump in a more comfortable position, depending on preference and body position.

Figure 18:
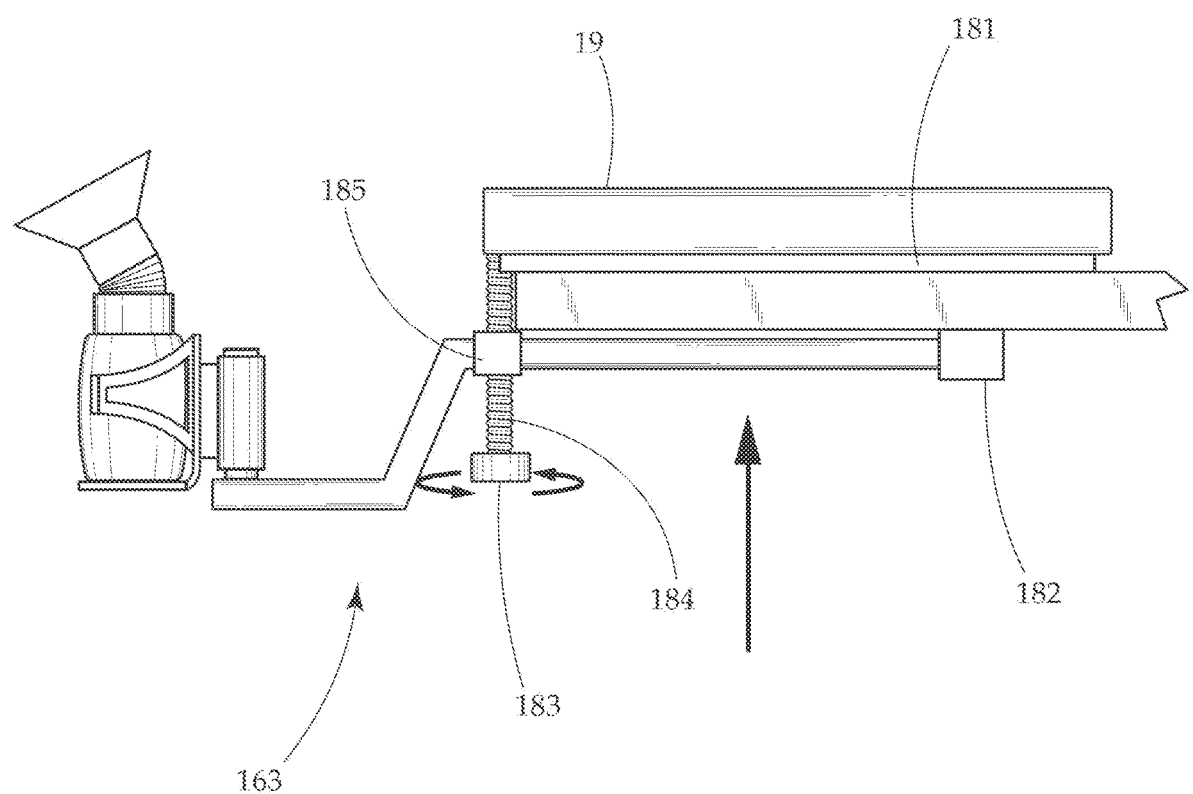
FIG. 18 provides a view of another embodiment of an adjustable shaft of a table of the breast pumping system.

FIG. 18 provides a view of another embodiment of connection of the shaft to the table. In this view, table 19 has a rubber spacer 181 around its perimeter. The rubber spacer provides for a stable resting point and high friction contact surface for whatever the table rests on. The shaft 163 is connected to the table 19 by a nut 185 which is threadedly engaged with a threaded connector 184 shaft. The shaft 163 can move lengthwise through the nut 185 to adjust the position of the bottle towards or away from the table 19 (moving left and right on the page). This movement may be any selectable movement such as via friction fit, a clamp, ratcheting motion, and the like. A knob 183 is rotatable to cause the threaded connector shaft 184 to rotate. This in turn causes a motion of the nut 185 which has threads engaged with the threaded shaft 184 moving the nut 185 and the shaft 163 which is connected to the nut 185 up and down to control a height of the bottle connected to shaft 163. In addition to adjustability, this configuration can operate as a clamp to hold the table 19 to a flat surface on which the table is resting such as a counter, table, desk, and the like. As seen in FIG. 18, a stopper 182 extends from the shaft 163 proximal end. The stopper engages a bottom side of the approximately flat surface on which the table is resting when the knob 183 is spun to urge the nut 185 upward towards the surface. A sufficient tightening of the stopper 182 against the surface by rotation of knob 183 will clamp the table 19 and stopper to the surface thereby holding the table 19 in a secure position. In many embodiments, the downwardly extending threaded shaft 184 is positioned at or close to a perimeter edge of the table 19 so that the majority of the table can rest on a surface, with an edge extending off the surface where the shaft 184 can extend downward as seen in FIG. 18. In further embodiments, the threaded shaft 184 may be hingedly connected to the table 19 to allow it to be folded inward, or covered/protected with a cover such as a rubber cover when not in use.

Figure 19:
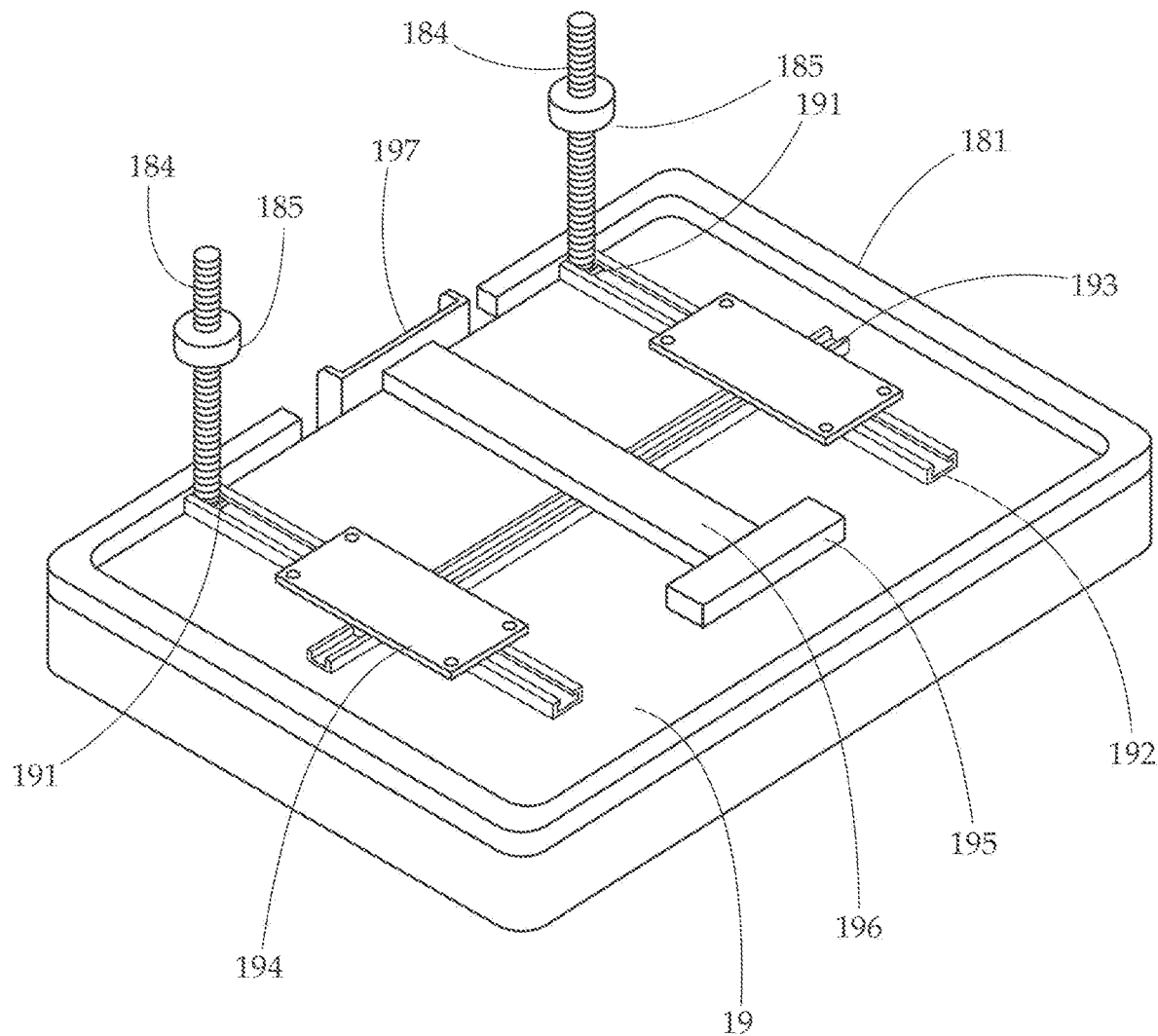
FIG. 19 provides a view of still another embodiment of the table of the breast pumping system.

FIG. 19 provides a bottom perspective view of another embodiment of the breast pumping system. This view shows the underside of the table and components allowing movable connection of the bottles to receive pumped milk and the table. A rubber perimeter spacer 181 extends around the edge of the table 19. Two threaded shafts 184 are connected to the table 19 at an edge via hinge 191. The hinge 191 is connected to a bar 192 which can move side to side along cross bar 193. In some cases, the bar 192 can also move forward and back towards and away from the lengthwise edge of the table 19. A bracket 194 slidably connects the bottle slider bar 192 to the cross bar 193. The threaded nut 185 is engaged with the shaft 184 and can receive the shaft for holding the bottle (not shown in this view). A bottom side of the headrest support base 197 is shown extending to the bottom of the table. A support bar 196 and anchor 195 connect to the base 197 and support the headrest while providing rigidity to the table 19 against the weight of the user's head and torso.

Figure 20:
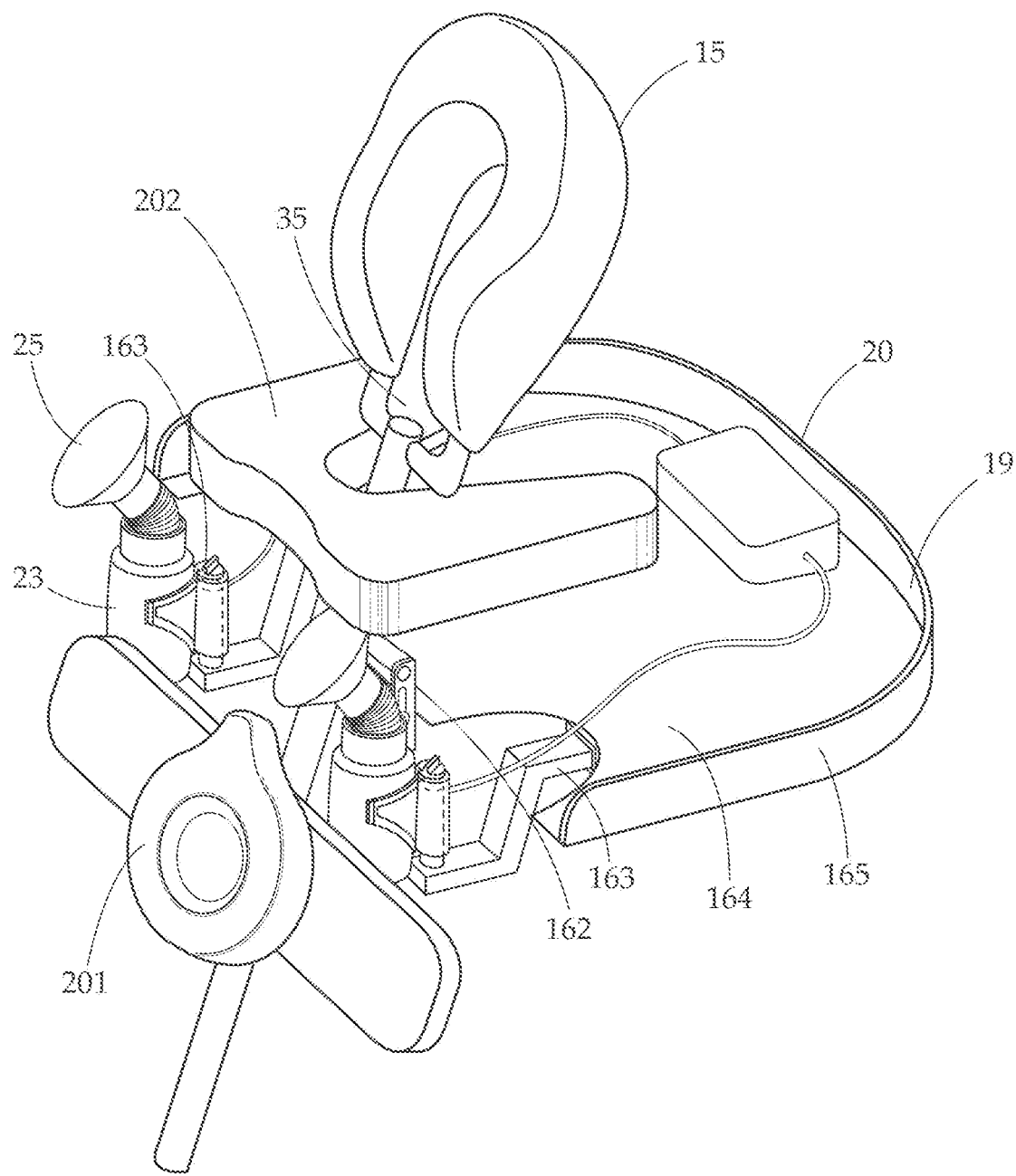
FIG. 20 provides a perspective view of yet another embodiment of a breast pumping chair.

FIG. 20 provides a perspective view of another embodiment of the breast pumping system. In this view, an integrated breast pumping chair is shown having a breast rest. However, it should be understood that the breast rest may also be applied in other embodiments including the breast pumping tables and other assemblies noted herein. The breast rest 202 is shown here as a two pronged platform with each prong having a flat or concave top surface to receive a breast. The prong portion tapers towards its distal end similarly to a breast. The breast rest 202 may be particularly helpful for nursing mothers to rest their breasts when not feeding or pumping to support them and allow fresh air to dry out the skin. In cases of mastitis or other infection, engorgement, clogged duct, weaning, and the like, the breasts can become uncomfortable, sensitive and painful. The breast rest 202 can help ease this discomfort by allowing the nursing woman to lie forward-leaning on the breast pumping chair having the breasts supported in a comfortable position. Optionally, ice, heat, cabbage, ointment or cream, and other treatments may be applied to ease the discomfort. The user is hands-free in this embodiment and no pumping bra is required. The user may also massage one or both breasts to manage any medical diagnoses. The breast rest 202 in this view is connected to central post 10. The breast pumping table 19 and all of its connected elements can be moved up and down and can move to a "pumping" position for breast pumping, or a "resting" position allowing the nursing woman to rest, for example by resting her breasts on the breast rest 202 and to encourage any necessary breast drainage. Similarly, the breast rest 202 may be adjustable in position, including height, and removable so as to not be in the way when pumping. Also, the bottles 23 may be removed from the bottle holders to make space for resting on the breast rest platform 202. For example, the bracket 175 may be removed from post 174 to create more space for a resting mode of operation. The breast rest 202 may be removable from the system and can in some embodiments be replaced with a grip for safety with the user mounting or dismounting the unit.

FIG. 20 also shows a view of a teardrop shaped pad 201. This pad is operable to distribute weight across an upper stomach area. This can be helpful for a post-partum mother to aid in comfort by not bearing too much weight on the lower abdomen. This is particularly useful for mothers who have had a caesarian section.

In a further embodiment, the forward leaning chair may be used in conjunction with a bassinet to efficiently and comfortably nurse a baby. The chair of the present disclosure positions the nursing mother in an optimal position for milk expression which may be used not only for pumping, but for direct nursing as well. The bassinet embodiment may be particularly useful for pre-term birth babies, babies who have had surgery or require a ventilator, IV, or other supplemental support because these babies cannot be easily moved and in some cases could be injured if moved. The inability of babies to be moved and in particular held closely during nursing makes direct breastfeeding very difficult if not impossible. This deprives the baby and mother of bonding time and a number of benefits provided by nursing which may be very beneficial to the baby when in such a fragile state. The device may also be advantageous for babies with sucking or latching difficulties by comfortably and ergonomically positioning both mother and baby. Thus, the forward leaning chair for nursing combined with the bassinet allows a mother to breast feed a fragile baby without disturbing the baby's healing position and/or tubes and lines that support the infant.

The bassinet contemplated herein may be connectable to the forward leaning chair in one embodiment, and may be positioned close to the forward leaning chair in a proper position for helping the baby latch to the mother's breast in another embodiment without necessarily connecting to the chair.

Figure 21:
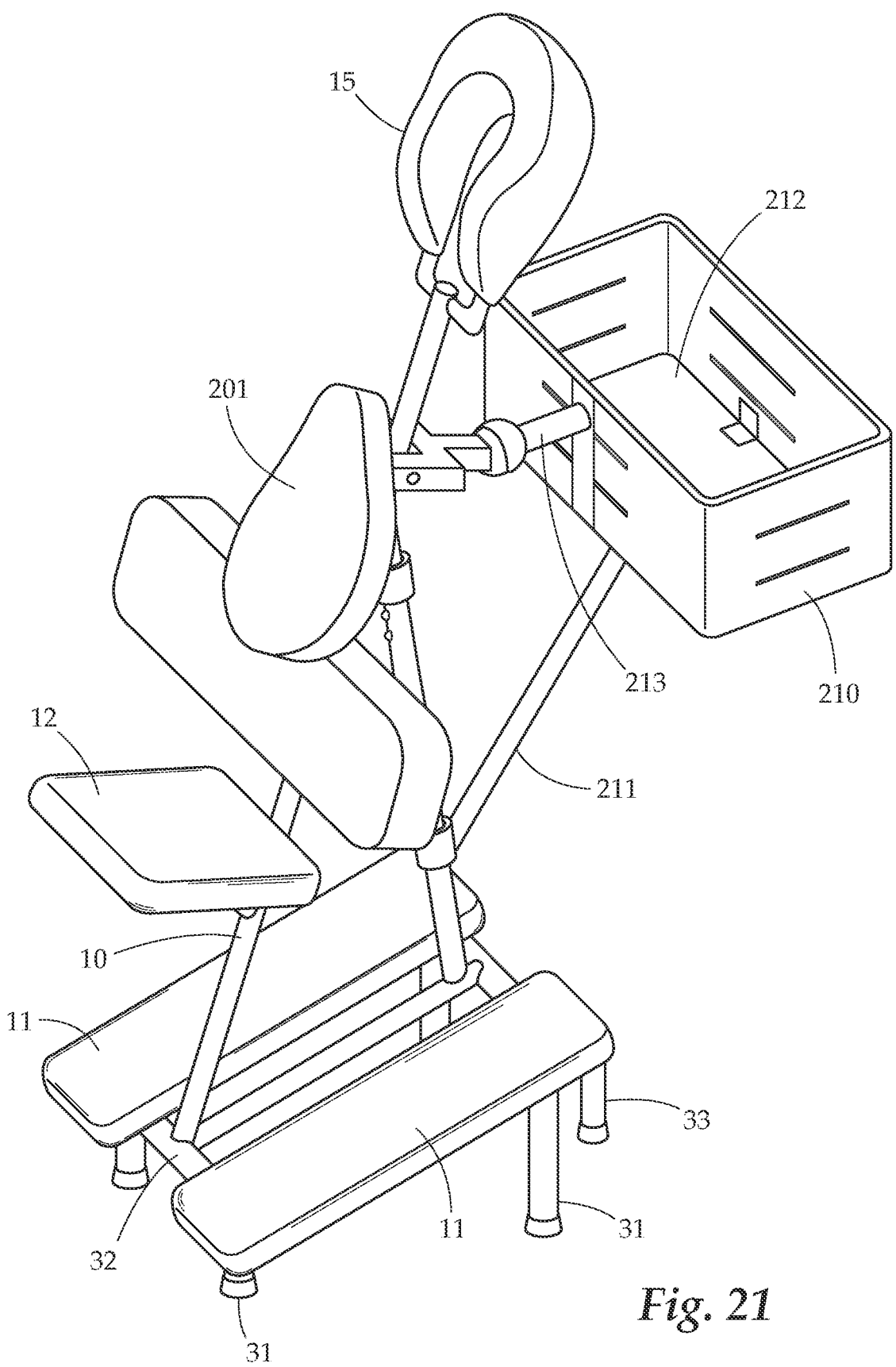
FIG. 21 provides a perspective view of yet still another embodiment of a breast pumping chair.

Turning now to FIG. 21, the forward leaning chair has a center post 10 to which the bassinet 210 is connected. In this embodiment, as in other embodiments, the chair utilizes shin pads 11, a base 31 supporting the chair, a head rest 15, and a stomach pad 201 for comfortable and ergonomic positioning of the nursing mother for optimal milk expression. The bassinet 210 has a base 212 and sidewalls. The bassinet 201 is connected to the chair, in this embodiment, via a support arm 211 and bracket 213. Support arm 211 and bracket 213 may be telescoping, bendable, or otherwise adjustable in length to allow for proper positioning of the bassinet 210. A ball and socket joint or similar pivoting joint may also be on the support arm 211. In many embodiments, a table for holding breast pumping supplies such as that shown in embodiments above may be removed and replaced with the bassinet using the same connection structures as for the table for holding breast pumping supplies. Further, in operation, due to the comfortable and hands-free nature of the system disclosed herein, the user may massage one or both breasts to manage possible medical issues and/or to increase the likelihood of more complete breast emptying during milk extraction.

Figure 22:
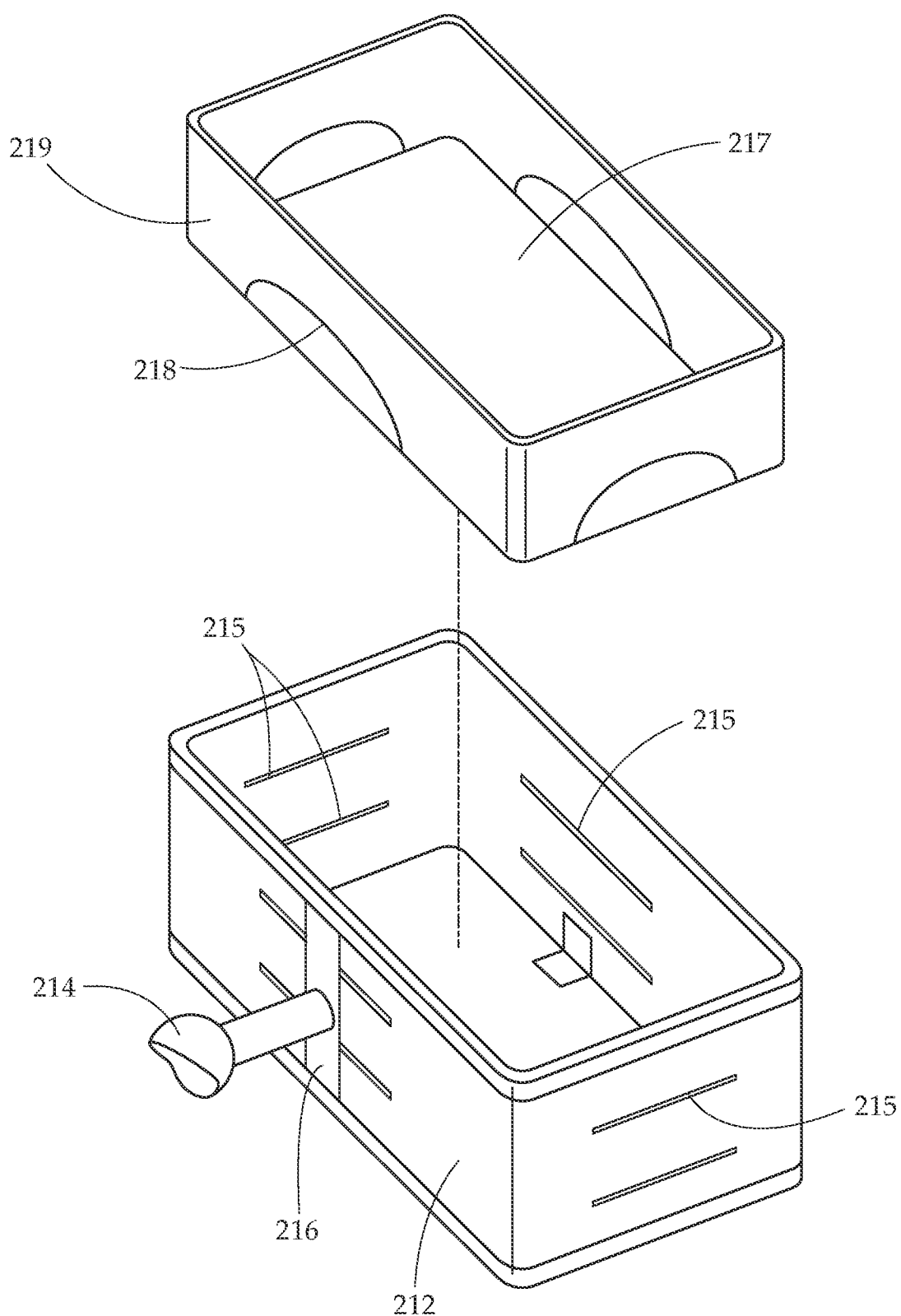
FIG. 22 provides a perspective view of an embodiment of a bassinet connectable to the forward leaning chair.

FIG. 22 shows one embodiment of the bassinet. In this embodiment, the bassinet 210 has adjustable connection points 215 which allow an adjustable height positioning of the bassinet bed 217. Raising and lowering the height allows the baby to be closer or further from the mother's body depending on size and positioning requirements. A connector 214 is removably connectable to a corresponding ball or pivot joint to allow for a pivoting or swiveling connection of the bassinet 210 to chair. Such motion allows for an optimal positioning of the baby relative to the breast and may allow for movement from one breast to the other without moving the baby or mother. Further, The connector 214 can be positioned at multiple heights along the height of the side wall at 216. A bassinet bed 217 is, in this embodiment, removable from the bassinet 210 for safe movement of the baby from the bassinet to another area such as an incubator, different bassinet, and the like. The bassinet bed 217 has sidewalls 219, and cutouts 218 which operate as handles to lift and move the bassinet bed 217.

Figure 23:
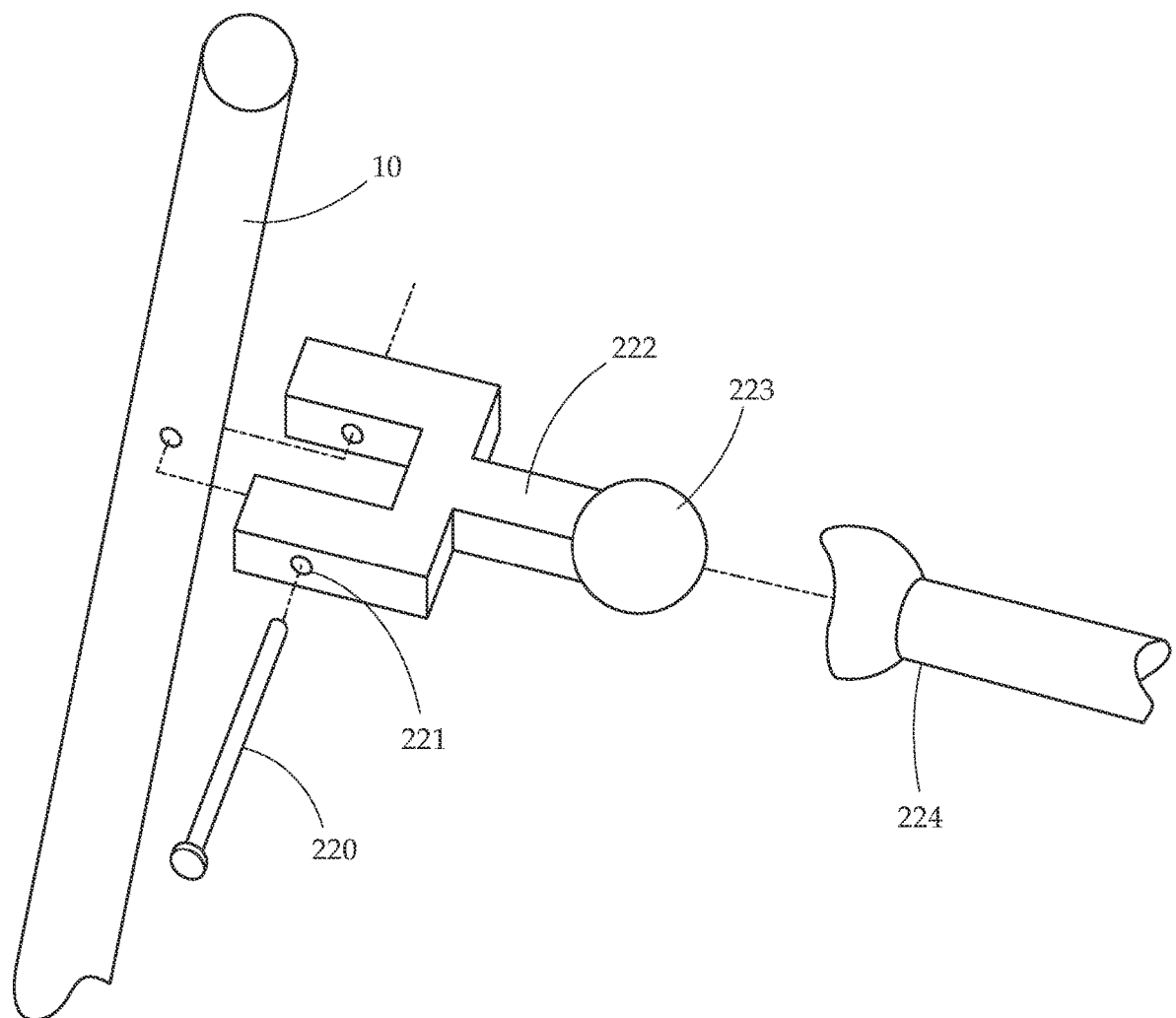
FIG. 23 provides a perspective view of yet another embodiment of a breast pumping chair.

FIG. 23 provides a view of an embodiment of a connector joining the post of the forward leaning chair to the bassinet. In this embodiment, the post 10 has a hole through its width. A bracket 222 has a U shape with arms which extend around the sides of the post 10. On the arms, holes 221 can align with the hole of the post 10. A pin 220 passes through holes 221 and the hole in the post 10 joining bracket 222 to post 10. Depending on embodiment, a spring loaded ball bearing may be positioned on a distal end of the pin 220 which prevents removal of the pin without application of sufficient force. Of course, other embodiments may use other structures to hold the pin 220 in place, such as a cotter pin and the like. On a distal end of the bracket is a connection ball 223. Other structures to connect the bracket 222 to bassinet may of course be used as well, including a direct connection of bracket to the bassinet. In the embodiment shown, the ball 223 connects to a corresponding ball joint 224 on the bassinet, allowing a rotational pivoting motion of the bassinet about the ball joint. It should be understood that there may be locking mechanism or mechanisms on any of the ball and socket joint (to stop or allow pivoting in a locked or unlocked mode, respectively) as well as on the posts which attach the bassinet to the chair to prevent accidental disconnection.

Figure 24:
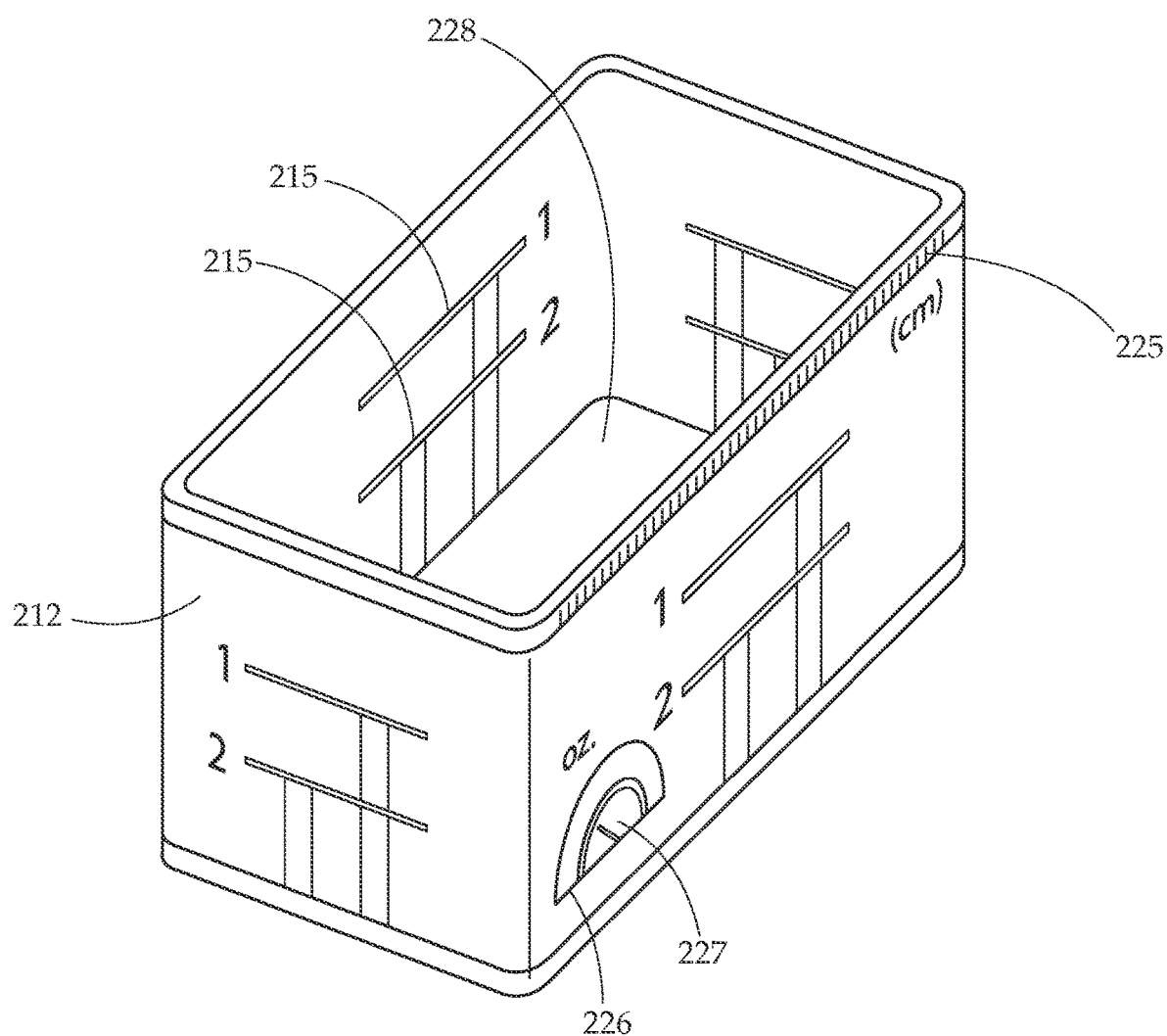
FIG. 24 provides a perspective view of another embodiment of a bassinet connectable to the forward leaning chair.

FIG. 24 provides another view of an embodiment of the bassinet. In this view, bassinet 210 has a base 212 formed of sidewalls and a bottom surface 228. A top lengthwise wall of the bassinet has measurement markings 225 as a ruler to aid in measuring the baby placed therein. Further, the bassinet may have a built-in scale 226 and display 227. The scale is useful to not only weight the baby but to measure how much milk the baby is consuming. By measuring the weight before and after feeding, the difference is the amount of milk given from mother to baby. Accordingly, the scale must be sensitive enough to measure even a small weight change corresponding to ounces down to a fraction of an ounce such as tenths of an ounce.

Figure 25:
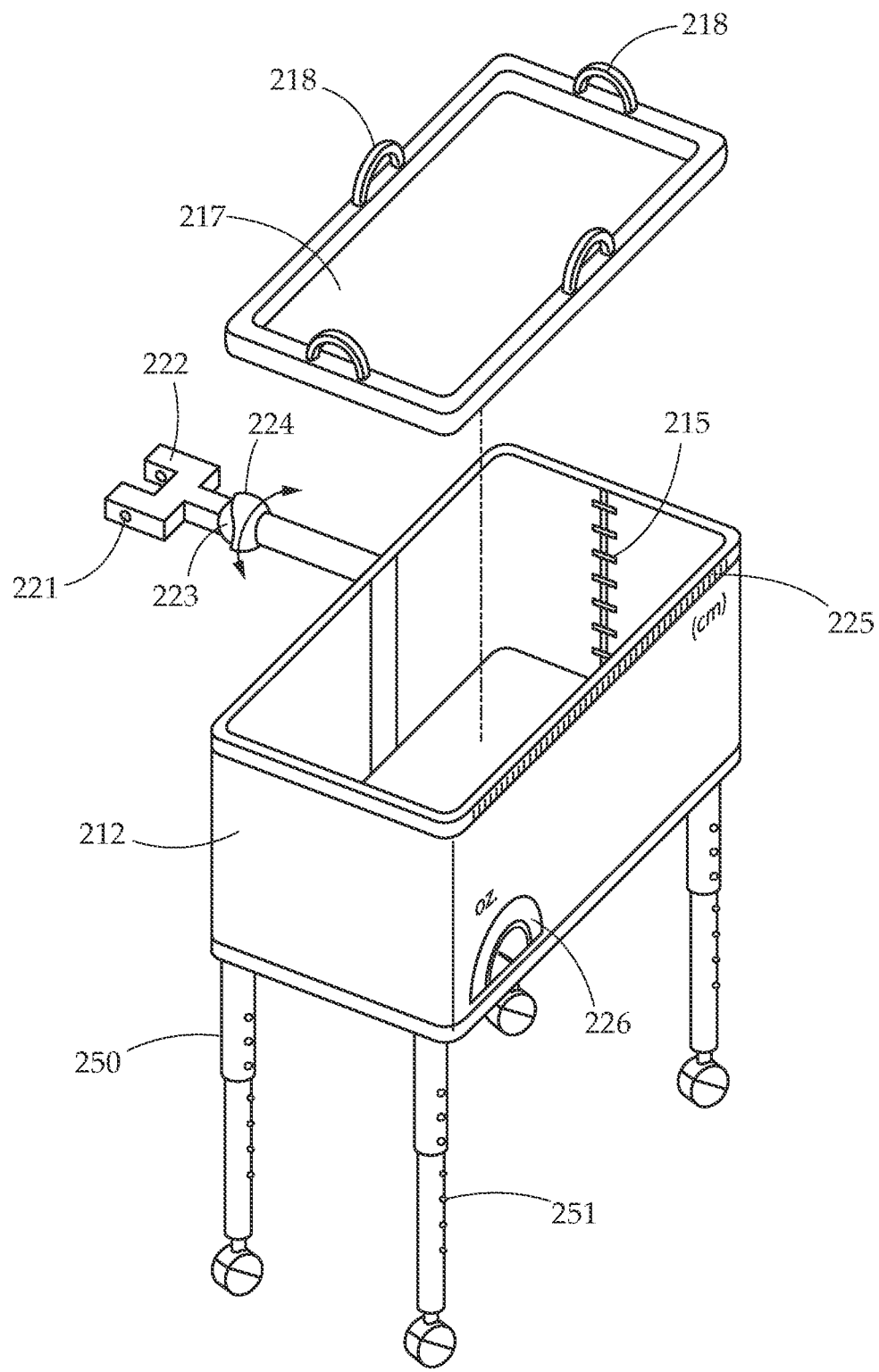
FIG. 25 provides a perspective view of an embodiment of still another embodiment of a bassinet connectable to the forward leaning chair.

FIG. 25 provides another embodiment of a bassinet which is supported on telescoping legs with optional casters. Here, the bassinet is connectable to the forward leaning chair in a manner as shown in FIG. 23, but of course other embodiments may have different connection arrangements. The bassinet 210 is supported by legs 250 which may be telescoping or have a length adjuster 251 formed by a pin which fits through one of a plurality of apertures. Lockable casters on the bottom of the legs allow rolling of the bassinet. A plurality of height adjustment connection points 215 allow adjustment of the height of the bed 217 which can be lifted by handles 218. A scale 226 on the side can weigh the baby and show amount of milk consumed. A top lengthwise wall of the bassinet has measurement markings 225 as a ruler to aid in measuring the baby placed therein. In operation, this embodiment may contain the infant within the bassinet, and when ready to feed, can be rolled over adjacent to the forward leaning chair. The bassinet may be connected to the chair for stability and safety purposes using connector bracket 222. Then, a mother may position herself on the forward leaning chair and commence breastfeeding to the infant in the bassinet.

In other embodiments, the bassinet may be on a slider to slide an edge of the bassinet from one breast to another. In many embodiments, height adjustment is possible in various manners to ensure proper placement of the infant relative to the mother's breast.

In some embodiments, the bassinet and/or bassinet bed may be transferrable between the bassinet, another bassinet for resting, an examination table, incubator, and the like.

While several variations of the present disclosure have been illustrated by way of example in preferred or particular embodiments, it is apparent that further embodiments could be developed within the spirit and scope of the present disclosure, or the inventive concept thereof. However, it is to be expressly understood that such modifications and adaptations are within the spirit and scope of the present disclosure, and are inclusive, but not limited to the following appended claims as set forth. As noted, the forward-leaning ergonomic feature of the inventive system allows for optimal breast milk expression.

What is claimed is:

1. A breast pumping system, comprising:
   a forward leaning chair operable to support a nursing mother in a forward-leaning position; and
   a bassinet connected to the forward leaning chair by a bracket of the bassinet connected to a central post of the forward leaning chair, wherein the bassinet comprises sidewalls and a bed of the bassinet is connectable to one of a plurality of different positions along the sidewalls to adjust a height of the bed.

2. The breast pumping system of claim 1, wherein the bassinet further comprises a plurality of legs supporting the bassinet.

3. The breast pumping system of claim 2, wherein a length of each of the plurality of legs is adjustable.

4. The breast pumping system of claim 2, wherein each of the plurality of legs further comprises a lockable caster.

5. The breast pumping system of claim 1, wherein the bassinet is further connected to the forward leaning chair by a support arm.

6. The breast pumping system of claim 1, wherein the bassinet is pivotally connected to the forward leaning chair.

7. The breast pumping system of claim 1, further comprising a head rest connected to the forward leaning chair.

8. The breast pumping system of claim 1, wherein the bassinet further comprises a scale operable to measure a weight of a baby in the bassinet.

9. The breast pumping system of claim 1, wherein the bassinet further comprises a plurality of length measurement markings along a length of at least one side of the bassinet.

10. The breast pumping system of claim 1, wherein the forward leaning chair further comprises a base, a post extending from the base, a seat, and a chest rest.

11. The breast pumping system of claim 1, wherein the bed is removable from the bassinet and the bed further comprises a plurality of handles.

12. The breast pumping system of claim 1, wherein the bassinet is connected to the post of the forward leaning chair and, while connected, is movable in a sliding motion in a widthwise direction relative to the forward leaning chair, allowing an infant in the bassinet to nurse from a left breast and right breast by the sliding motion of the bassinet.

13. A breast pumping system, comprising:
  a chair operable to support a user in a forward-leaning position; and
  a bassinet connected to the chair by a bracket of the bassinet connected to a central post of the chair, wherein the bassinet comprises sidewalls and a bed of the bassinet disposed proximate the sidewalls.

14. The breast pumping system of claim 13, wherein the bassinet further comprises a scale operable to measure a weight of a baby in the bassinet.

15. The breast pumping system of claim 13, wherein the bassinet further comprises a plurality of length measurement markings along a length of one or more of the sidewalls.

16. A breast pumping system, comprising:
  a forward-leaning chair comprising a base, a post extending from the base, a seat, and a chest rest coupled to the post; and
  a bassinet connected to the post and comprising sidewalls and a removable bed configured to be disposed within the bassinet and proximate the sidewalls.

17. The breast pumping system of claim 16, wherein the bassinet further comprises a scale operable to measure a weight of a baby in the bassinet.

18. The breast pumping system of claim 16, wherein the bassinet further comprises a plurality of length measurement markings along a length of one or more of the sidewalls.

19. The breast pumping system of claim 16, wherein the bassinet is connected to the post by a bracket.

* * * * *